United States Patent
Kim et al.

(10) Patent No.: US 10,071,170 B2
(45) Date of Patent: Sep. 11, 2018

(54) ANTIBODY-DRUG CONJUGATE HAVING IMPROVED STABILITY AND USE THEREOF

(71) Applicant: ABLBIO, Seoul (KR)

(72) Inventors: Young Min Kim, Gyeonggi-do (KR); Min Ji Ko, Daejeon (KR); Jae Yong Kim, Seoul (KR); Ju Hee Kim, Daejeon (KR); Kyung Duk Moon, Daejeon (KR); Dae Hae Song, Daejeon (KR); Jae Hyun Eom, Sejong (KR); Jin Won Jung, Dajeon (KR)

(73) Assignee: ABLBIO, Seoul (KR)

( * ) Notice: Subject to any disclaimer, the term of this patent is extended or adjusted under 35 U.S.C. 154(b) by 0 days.

(21) Appl. No.: 14/898,126

(22) PCT Filed: Jun. 24, 2014

(86) PCT No.: PCT/KR2014/005589
§ 371 (c)(1),
(2) Date: Dec. 12, 2015

(87) PCT Pub. No.: WO2014/208987
PCT Pub. Date: Dec. 31, 2014

(65) Prior Publication Data
US 2016/0136300 A1    May 19, 2016

(30) Foreign Application Priority Data

Jun. 24, 2013 (KR) .................... 10-2013-0072686

(51) Int. Cl.
| | | |
|---|---|---|
| C07K 16/30 | (2006.01) | |
| A61K 47/48 | (2006.01) | |
| C07K 16/28 | (2006.01) | |
| C07K 16/32 | (2006.01) | |
| A61K 47/68 | (2017.01) | |
| A61K 39/00 | (2006.01) | |

(52) U.S. Cl.
CPC .... *A61K 47/48646* (2013.01); *A61K 47/6803* (2017.08); *A61K 47/6817* (2017.08); *A61K 47/6849* (2017.08); *A61K 47/6851* (2017.08); *C07K 16/2803* (2013.01); *C07K 16/2878* (2013.01); *C07K 16/32* (2013.01); *A61K 2039/505* (2013.01); *C07K 2317/24* (2013.01); *C07K 2317/56* (2013.01); *C07K 2317/73* (2013.01); *C07K 2317/92* (2013.01); *C07K 2317/94* (2013.01)

(58) Field of Classification Search
CPC .............................. A61K 47/48; C07K 16/30
USPC ................... 424/183.1; 530/391.7
See application file for complete search history.

(56) References Cited

U.S. PATENT DOCUMENTS

| | | | |
|---|---|---|---|
| 7,723,485 B2 | 5/2010 | Junutula et al. | |
| 2003/0215421 A1 | 11/2003 | McDonald et al. | |
| 2004/0019157 A1* | 1/2004 | Won | C08G 65/324 525/403 |
| 2005/0276812 A1 | 12/2005 | Ebens, Jr. et al. | |
| 2006/0193865 A1* | 8/2006 | Govindan | C07K 16/1063 424/155.1 |
| 2010/0183636 A1 | 7/2010 | Law et al. | |
| 2010/0310573 A1* | 12/2010 | Nakagawa | C07K 16/2812 424/144.1 |
| 2011/0085970 A1 | 4/2011 | Terrett | |
| 2011/0171125 A1 | 7/2011 | Elkins | |
| 2013/0251712 A1* | 9/2013 | Zwaagstra | A61K 47/48369 424/133.1 |
| 2013/0295007 A1* | 11/2013 | Chen | A61K 39/39558 424/1.49 |
| 2013/0309257 A1* | 11/2013 | Giulio | A61K 47/48438 424/181.1 |

FOREIGN PATENT DOCUMENTS

| | | |
|---|---|---|
| EP | 3096141 A1 | 11/2016 |
| KR | 10-2007-0037575 A | 4/2007 |
| KR | 10-2013-0138608 A | 12/2013 |
| WO | 9116071 A1 | 10/1991 |
| WO | 0021573 A1 | 4/2000 |
| WO | 0162998 A1 | 8/2001 |
| WO | 2005037992 A2 | 4/2005 |
| WO | 2005117986 A2 | 12/2005 |
| WO | 2007109254 A2 | 9/2007 |
| WO | 2007124463 A1 | 11/2007 |
| WO | 2007140371 A2 | 12/2007 |
| WO | 2008019817 A1 | 2/2008 |
| WO | 2008036449 A2 | 3/2008 |
| WO | 2009026274 A1 | 2/2009 |
| WO | 2009100029 A1 | 8/2009 |
| WO | 2010123012 A1 | 10/2010 |
| WO | 2012104344 A1 | 8/2012 |
| WO | 2013032032 A1 | 3/2013 |
| WO | 2013122950 A1 | 8/2013 |

(Continued)

OTHER PUBLICATIONS

Tripathi et al. (Current Organic Chem 2008, 12: 1093-1115).*

(Continued)

*Primary Examiner* — Yan Xiao

(74) *Attorney, Agent, or Firm* — Hultquist, PLLC; Steven J. Hultquist

(57) ABSTRACT

The present invention relates to an antibody-drug conjugate comprising a drug conjugated to an antibody, a preparation method thereof and the use thereof.

11 Claims, 18 Drawing Sheets

Specification includes a Sequence Listing.

(56) References Cited

FOREIGN PATENT DOCUMENTS

WO     2015005553 A1     1/2015

OTHER PUBLICATIONS

Zolot, R., et al., "Antibody-drug conjugates", Nature Reviews: Drug Discovery, Apr. 2013, pp. 259-260, vol. 12.

Chih, H.-W., et al., "Identification of Amino Acid Residues Responsible for the Release of Free Drug from an Antibody-Drug Conjugate Utilizing Lysine-Succinimidyl Ester Chemistry", "Journal of Pharmaceutical Sciences", Jul. 2011, pp. 2518-2525, vol. 100, No. 7.

Hamann, P.R., et al., "Gemtuzumab Ozogamicin, A Potent and Selective Anti-CD33 Antibody-Calicheamicin Conjugate for Treatment of Acute Myeloid Leukemia", "Bioconjugate Chemistry", Dec. 19, 2001, pp. 47-58, vol. 13, No. 1.

Kalkhof, S., et al., "Chances and pitfalls of chemical cross-linking with amine-reactive N-hydroxysuccinimide esters", "Analytical and Bioanalytical Chemistry", Jul. 27, 2008, pp. 305-312, vol. 392.

Madler, S., et al., "Chemical cross-linking with NHS esters: a systematic study on amino acid reactivities", "Journal of Mass Spectrometry", Jan. 8, 2009, pp. 694-706, vol. 44.

Casi, G., et al., "Site-Specific Traceless Coupling of Potent Cytotoxic Drugs to Recombinant Antibodies for Pharmacodelivery", "Journal of the American Chemical Society", Mar. 6, 2012, pp. 5887-5892, vol. 134, No. 13.

Gianolio, D.A., et al., "Targeting HER2-positive Cancer with Dolastatin 15 Derivatives Conjugated to Trastuzumab, Novel Antibody-drug Conjugates", "Cancer Chemotherapy and Pharmacology", Jul. 22, 2012, pp. 439-449, vol. 70, No. 3.

Michaelson, J.S., et al., "Anti-tumor Activity of Stability-engineered IgG-like Bispecific Antibodies Targeting Trail-R2 and LTR", "mAbs", Mar. 1, 2009, pp. 128-141, vol. 1, No. 2, Publisher: Landes Bioscience.

Rana, T.M., et al., "N-Terminal Modification of Immunoglobulin Polypeptide Chains Tagged with Isothiocyanato Chelates", "Bioconjugate Chemistry", Jul. 25, 1990, pp. 357-362, vol. 1, No. 5.

Scheck, R.A., et al., "Regioselective Labeling of Antibodies through N-Terminal Transamination", "ACS Chemical Biology", Apr. 13, 2007, pp. 247-251, vol. 2, No. 4.

Seeger, H., Blutuntersuchung im Dunkelfeld und ihre Glaubwurdigkeit, URL:https://www.dunkelfeld-blutdiagnostik.de/cms/NS_Blutuntersuchung-im-Dunkelfeld-G 1aubwuerdigkeit.html, Nov. 11, 2007.

Seeger, H., Blutuntersuchung im Dunkelfeld und ihre Glaubwurdigkeit, URL:https://www.dunkelfeld-blutdiagnostik.de/cms/NS_Blutuntersuchung-im-Dunkelfeld-G 1aubwuerdigkeit.html, Nov. 11, 2007, Page(s) Machine Translation.

\* cited by examiner

SEQUENCE LISTING

```
<160> NUMBER OF SEQ ID NOS: 3

<210> SEQ ID NO 1
<211> LENGTH: 19
<212> TYPE: PRT
<213> ORGANISM: Artificial Sequence
<220> FEATURE:
<223> OTHER INFORMATION: Trypsin fragment (heavy chain N-term)

<400> SEQUENCE: 1

Glu Val Gln Leu Val Glu Ser Gly Gly Gly Leu Val Gln Pro Gly Gly
1               5                   10                  15

Ser Leu Arg

<210> SEQ ID NO 2
<211> LENGTH: 18
<212> TYPE: PRT
<213> ORGANISM: Artificial Sequence
<220> FEATURE:
<223> OTHER INFORMATION: Trypsin fragment (light chain N-term)

<400> SEQUENCE: 2

Asp Ile Gln Met Thr Gln Ser Pro Ser Ser Leu Ser Ala Ser Val Gly
1               5                   10                  15

Asp Arg

<210> SEQ ID NO 3
<211> LENGTH: 33
<212> TYPE: PRT
<213> ORGANISM: Artificial Sequence
<220> FEATURE:
<223> OTHER INFORMATION: Trypsin fragment (heavy chain-CH2)

<400> SEQUENCE: 3

Thr His Thr Cys Pro Pro Cys Pro Ala Pro Glu Leu Leu Gly Gly Pro
1               5                   10                  15
```

-continued

```
Ser Val Phe Leu Phe Pro Pro Lys Pro Lys Asp Thr Leu Met Ile Ser
            20                  25                  30
Arg
```

ANTIBODY-DRUG CONJUGATE HAVING IMPROVED STABILITY AND USE THEREOF

CROSS-REFERENCE TO RELATED APPLICATIONS

This application is a U.S. national phase under the provisions of 35 U.S.C. § 371 of International Patent Application No. PCT/KR14/05589 filed Jun. 24, 2014, which in turn claims priority of Korean Patent Application No. 10-2013-0072686 filed Jun. 24, 2013. The disclosures of such international patent application and Korean priority patent application are hereby incorporated herein by reference in their respective entireties, for all purposes.

TECHNICAL FIELD

The present invention relates to an antibody-drug conjugate comprising a drug conjugated to the N-terminal amino acid residue of the heavy chain or light chain of an antibody, a preparation method thereof, and the use thereof.

BACKGROUND ART

In recent years, methods of diagnosing or treating various diseases using antibodies have been studied. Particularly, because of the target specificity of antibodies, various therapeutic methods using antibodies have been developed, and various types of drugs containing antibodies, for example, antibody-drug conjugates (ADCs), have been developed. Thus, studies have been continuously conducted to increase the in vivo stability of antibodies or antibody-drug conjugates and maximize the therapeutic effects thereof.

Among them, antibody-drug conjugates generally have the disadvantage of low in vivo stability compared to natural antibodies, but have been developed in order to overcome the disadvantages (low therapeutic effects) of natural antibodies by conjugating them to drugs. Various antibody-drug conjugates in which drugs having certain medical effects, such as cytotoxin, are conjugated to target-specific antibodies, have been developed. In particular, a method of inducing cancer cell death by cytotoxin conjugated to a cancer cell-specific antibody is a method that is actually currently used.

However, such antibody-drug conjugates generally have low in vivo stability compared to natural antibodies. Furthermore, if drug antibody ratio (DAR) is increased in order to increase therapeutic effects, there will be various technical problems to be solved. First, an increase in drug antibody ratio should not interfere with the antigen-binding ability and Fc function of antibodies for target-specific therapy, should lead to an increase in therapeutic effects, and should not reduce the in vivo stability (i.e., blood half-life) of antibody-drug conjugates. The object of the current antibody-drug conjugate preparation field is to maintain the highest possible antibody drug ratio in view of the above-described technical problems. In particular, considering that the expression level of cancer cell surface antigens is low, the highest possible drug antibody ratio (DAR) should be maintained in order to maintain high cytotoxicity. However, if DAR reaches 8, there is a problem in that the blood half-life of the antibody-drug conjugate decreases due to the effect of the hydrophobic drug conjugated to the antibody so that the toxicity thereof can increase and in vivo efficacy thereof can decrease.

Under this background, the present inventors have made extensive efforts to develop a technology capable of preparing an antibody-drug conjugate which maintains the antigen-binding activity of a parent antibody, exhibits excellent anticancer effects, and has low drug toxicity and excellent in vivo efficacy. As a result, the present inventors have found that, when a drug is conjugated to the N-terminus of the heavy chain or light chain of an antibody, the antibody-drug conjugate has excellent blood stability and anticancer activity while having low in vivo toxicity compared to previously reported antibody-drug conjugates, thereby completing the present invention.

DISCLOSURE OF INVENTION

It is an object of the present invention to provide an antibody-drug conjugate comprising a drug conjugated to the N-terminal amino acid residue of the heavy chain or light chain of an antibody.

Another object of the present invention is to provide a method for preparing the above antibody-drug conjugate.

Still another object of the present invention is to provide a composition comprising the above antibody-drug conjugate.

Yet another object of the present invention is to provide a method for treating cancer, comprising administering the above antibody-drug conjugate to a subject suspected of having cancer.

A further object of the present invention is to provide a method for treating autoimmune disease, comprising administering the above antibody-drug conjugate to a subject suspected of having autoimmune disease.

A still further object of the present invention is to provide a method for screening an antibody suitable for use in preparation of the above antibody-drug conjugate.

Advantageous Effects

A method for preparing an antibody-drug conjugate according to the present invention can prepare an antibody-drug conjugate having higher in vivo efficacy, stability and lower toxicity.

BEST MODE FOR CARRYING OUT THE INVENTION

In one aspect, the present invention provides is directed to an antibody-drug conjugate comprising a drug conjugated to the N-terminal amino acid residue of the heavy chain or light chain of an antibody.

Figure 2:
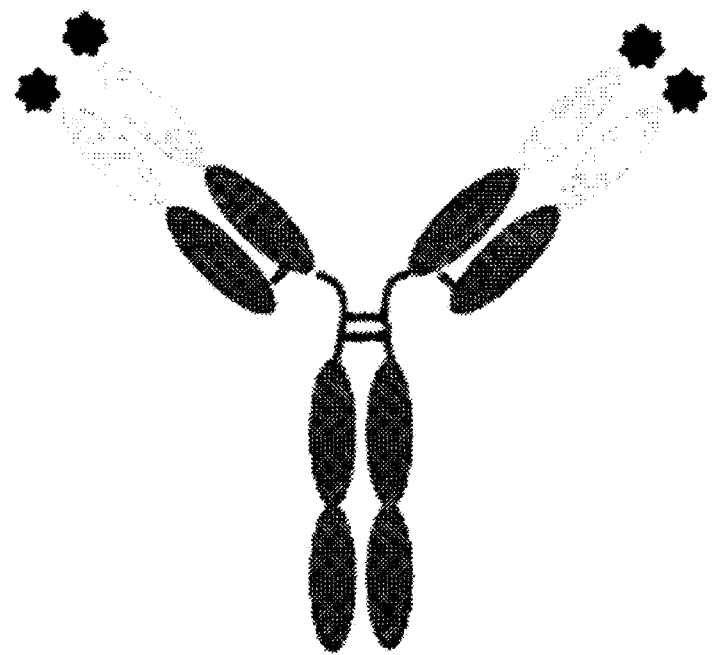
FIG. 2 is a schematic diagram showing the structure of a non-genetically modified monoclonal antibody-cytotoxin conjugate in which the number and site of cytotoxin moieties conjugated to an antibody are homogeneous.

As used herein, the term "antibody-drug conjugate (ADC)" refers to the form in which a drug and an antibody are chemically conjugated to each other without reducing the biological activities of the antibody and the drugs. In the present invention, the term "antibody-drug conjugate" refers to the form in which the drug is conjugated to the N-terminal amino acid residue of the heavy chain and/or light chain of the antibody, particularly, the form in which the drug is conjugated to the N-terminal α-amine group of the heavy chain and/or light chain of the antibody. In the present invention, it was found that, when a drug was site-specifically conjugated to the N-terminus of the heavy chain or light chain among various regions of an antibody, the antibody-drug conjugate had excellent in vivo efficacy and stability and low toxicity, compared to previously reported antibody-drug conjugates, including antibody-drug conjugates formed by cysteine conjugation, antibody-drug conjugates formed by thiol conjugation, and antibody-drug conjugates formed by lysine conjugation, indicating that the N-terminus of the heavy chain or light chain of antibodies can be a site advantageous in terms of efficacy, stability and low toxicity. This schematic view of an antibody-drug conjugate according to the present invention is schematically shown in FIG. 2.

As used herein, the term "N-terminus" refers to the amino terminus (N-terminus) of the heavy chain or light chain of an antibody, which is a site to which a drug can be conjugated for the purpose of the present invention. Examples of the N-terminus include, but are not limited to, not only amino acid residues at the distal end of the N-terminus, but also amino acid residues near the N-terminus. Specifically, the term "N-terminus" refers to the first amino acid residue of the heavy chain or light chain of an antibody, and more specifically, refers to the α-amine group of the first amino acid of the heavy chain or light chain of an antibody, but is not limited thereto.

The antibody-drug conjugate according to the present invention can have the advantage of guaranteeing homogeneity through the site-specific conjugation or number-specific conjugation between an antibody and a drug. Particularly, through the optimization procedure of the present invention, 1-8 drug moieties corresponding to the optimal drug-antibody ratio (DAR) can be conjugated to the N-terminal amino acid residue of each antibody molecule.

As used herein, the term "homogeneity" refers to the case in which the ratio and site of conjugation between two substances in a conjugate of the two substances are homogeneous. However, the term is intended to include not only the case in which the ratio and site of conjugation are completely homogeneous, but also the case in which a specific ratio and site of conjugation are predominant. When a conjugate has homogeneity, it is entirely homogeneous, and the dose-dependent efficacy thereof can be accurately measured, and thus the dose and number of administration thereof can be standardized.

As used herein, the term "antibody" means a protein molecule which comprises an immunoglobulin molecule immunologically reactive with a certain antigen, and which serves as a receptor that specifically recognizes the antigen. The term is intended to encompass polyclonal antibodies, monoclonal antibodies, full-length antibodies and antibody fragments containing antigen binding domains. A full-length antibody has two full-length light chains and two full-length heavy chains, in which each of the light chains is linked to the heavy chain by a disulfide bond. The full-length antibody comprises IgA, IgD, IgE, IgM and IgG, and subtypes of IgG include IgG1, IgG2, IgG3 and IgG4. The term "antibody fragment" refers to a fragment having an antigen-binding function, and is intended to include Fab, Fab', F(ab')$_2$, scFv and Fv. Fab comprises light-chain and heavy-chain variable regions, a light-chain constant region, and a heavy-chain first constant domain (CH1), and has one antigen-binding site. Fab' differs from Fab in that it has a hinge region including one or more cysteine residues at the C-terminus of the heavy-chain CH1 domain. An F(ab')$_2$ antibody is formed by a disulfide bond between the cysteine residues of the hinge region of Fab'. Fv means a minimal antibody fragment having only a heavy-chain variable region and a light-chain variable region. dsFv is has a structure in which a heavy-chain variable region and a light-chain variable region are linked to each other by a disulfide bond, and scFV generally has a structure in which a heavy-chain variable region and a light-chain variable region are covalently linked to each other by a peptide linker. These antibody fragments can be obtained using proteases (for example, Fab fragments can be obtained by digesting a full-length antibody with papain, and F(ab')$_2$ fragments can be obtained by digesting a full-length antibody with pepsin). Preferably, these antibody fragments can be produced by a genetic recombinant technique. These antibody fragments can be obtained using proteases (for example, digestion of a whole antibody with papain or pepsin affords Fab or F(ab')2, respectively), and preferably may be constructed by genetic recombination techniques.

In addition, the antibody that is used in the present invention may be a natural antibody or a recombinant antibody. As used herein, the term "natural antibody" refers to an antibody that has undergone no genetic modification. The natural antibody may have a significantly low risk of immunogenicity, unlike antibodies genetically modified in vivo. As used herein, the term "recombinant antibody" means a genetically modified antibody which may have an antigen-binding activity or desired characteristic imparted by genetic modification.

As used herein, the term "genetic modification" refers to an action of changing the amino acid sequence of interest and is intended to include the modification of polypeptides having amino acid sequences that somewhat differ from the amino acid sequence of a native sequence polypeptide encoding the amino acid sequence of interest. Amino acid sequence variants contain an amino acid sequence having a substitution, deletion or insertion of one or more amino acid residues at one or more specific positions in a native amino acid sequence.

The antibody that is used in the present invention may be an antibody recognizing a cell surface antigen which is internalized into cells when binding to the antibody. For the purpose of the present invention, when an antigen is internalized into cells by binding to the antibody, a drug, particularly a cytotoxic drug, conjugated to the antibody, can enter the cells due to the characteristics of the antibody, and thus can exhibit high efficacy, but is not limited thereto.

In addition, the antibody that is used in the present invention may be an antibody that binds specifically to a cancer cell surface antigen or a surface antigen of a tissue in which an autoimmune disease has occurred.

As used herein, the term "cancer cell surface antigen" refers to either a substance that is not produced in normal cells or not exposed to the cell surface, or a substance that is exposed to the cell surface specifically in cancer cells, or s substance that is present more on the surface of cancer cells than on the surface of normal cells. When the substance of interest is recognized by the antibody, it is referred to as an antigen.

Specifically, the cancer cell surface antigen that is used I the present invention may be any cancer cell surface antigen that can be recognized specifically by the antibody of the present invention. Examples of the cancer cell surface antigen may include CD19, CD20, CD30, CD33, CD37, CD22, CD56, CD70, CD74, CD138, Muc-16, mesothelin, HER2, HER3, GPNMB (glycoprotein NMB), IGF-1R, BCMA (B cell maturation antigen), PSMA (prostate-specific membrane antigen), EpCAM (Epithelial cell adhesion molecule), and EGFR (epidermal growth factor receptor). More specifically, the cancer cell surface antigen may be any one selected from the group consisting of HER2, CD30, CD56, and GPNMB, but is not limited thereto. In an example of the present invention, Trastuzumab, a kind of anti-HER2 antibody, Lorvotuzumab, a kind of anti-CD56 antibody, Brentuximab, a kind of anti-CD30 antibody, and Glembatumumab, a kind of anti-GPNMB antibody, which recognize Her2, CD56 and GPNMB, were used as model antibodies.

As used herein, the term "drug" means any substance having cell-specific biological activity, and is intended to include compounds, DNA, RNA, peptides and the like. The term "drug" is intended to include not only substances containing a reactive group capable of crosslinking with an α-amine group, but also substances having a linker containing a reactive group capable of crosslinking with an α-amine group. In this case, the drug can bind site-specifically to the N-terminal amino acid residue of the antibody by the linker, but is not limited thereto.

The term "linker" refers to a chemical moiety comprising an atomic chain that allows the drug to bind covalently to the antibody. The linker is prepared in a state in which it is connected to the drug, and the end of the linker has a reactive group that can be linked to the antibody.

Examples of the reactive group capable of crosslinking with an α-amine group include any reactive groups known in the art, which can crosslink with the N-terminal α-amine group of the heavy chain or light chain of the antibody. Examples of the reactive group may include isothiocyanate, isocyanate, acyl azide, NHS ester, sulfonyl chloride, aldehyde, glyoxal, epoxide, oxirane, carbonate, aryl halide, imidoester, carbodiimide, anhydride, and fluorophenyl ester. More preferably, the reactive group is aldehyde or NHS ester, but not specifically limited thereto. Such reactive groups can be bound with the amine group by acylation or alkylation, but are not specifically limited thereto.

In particular, the antibody-drug conjugate of the present invention may be an immunoconjugate in which the drug connected with a linker having a reactive aldehyde group is conjugated to the N-terminal amino acid residue of the antibody in a site-specific and number-specific way.

The reactive aldehyde group is effective in site-specifically conjugating the drug to the N-terminal amino acid residue (particularly α-amine) of the antibody while minimizing non-specific reactions. The final product produced through reductive alkylation by an aldehyde bond is much more stable than that linked by an amide bond. The reactive aldehyde group has the property of selectively reacting with the N-terminal α-amine at low pH. Thus, the conjugate of the present invention has homogeneous in that the drug is site-specifically conjugated to the N-terminal α-amine of the antibody. Thus, the present invention overcomes the problem of the prior art in which the uniform efficacy and quality of a drug cannot be guaranteed because of heterogeneity of the number and site of conjugations in conventional antibody-drug conjugates, but is not specifically limited thereto.

In an example of the present invention, the present inventors have found that, when a conjugation reaction is carried out at a pH of 6.0 or lower in order to conjugate a cytotoxic drug site-specifically to the α-amine of an antibody, the conjugation of the cytotoxic drug to the ε-amine of lysine residues can be minimized.

The drug that is used in the present invention may be any substance that can induce the activation or inhibition of certain signaling pathways, including cell death, cell proliferation, immune activation and immune suppression. In particular, the drug may be a cytotoxic drug or an immunosuppressive agent.

As used herein, the term "cytotoxic drug" refers to any substance, for example, a compound, which has a cytotoxic or cell proliferation inhibitory effect. The term "cytotoxic effect" refers to the effect of inhibiting or reducing the function of cells to induce disruption of the cells, and the term "cell proliferation inhibitory effect" refers to the effect of limiting cell growth functions such as cell growth or cell proliferation.

Examples of the cytotoxic drug that is used in the present invention include chemotherapeutic agents, including microtubule structure formation inhibitors, meiosis inhibitors, RNA polymerase inhibitors, topoisomerase inhibitors, DNA intercalators, DNA alkylators and ribosome inhibitors, protein toxins that can function as enzymes, and radioisotopes. Examples of the cytotoxic drug may include maytansinoid, auristatin, dolastatin, tubulysin, calicheamicin, pyrrolobenzodiazepines, doxorubicin, duocamycin, carboplatin(paraplatin), cisplatin, cyclophosphamide, ifosfamide, nidran, [nitrogen mustard(mechlorethamine HCL)], bleomycin, mitomycin C, cytarabine, fluorouracil, gemcitabine, trimetrexate, methotrexate, etoposide, vinblastine, vinorelbine, alimta, altretamine, procarbazine, taxol, taxotere, topotecan, irinotecan, trichothecene, CC1065, alpha-amanitin, other enediyne antibiotics, exotoxin, and plant toxin. In addition, compounds include their stereoisomers and derivatives. Furthermore, the auristatin that is used in the present invention may be monomethyl auristatin E or monomethyl auristatin F, but is not limited thereto.

The term "immunosuppressive agent" refers to any compound having the effect of reducing immune responses. The term means a substance that can antagonize immune causing substances or that can inhibit substances (cytokines such as interleukins) which are involved in immune responses.

In an example of the present invention, Trastuzumab, Lorvotuzumab, Brentuximab and Glembatumumab were used as model antibodies, and monomethyl auristatin E ((MMAE)) or monomethyl auristatin F (MMAF) were used as cytotoxic drugs to be conjugated to the N-terminus of the antibodies (Examples 1 and 2). Trastuzumab was allowed to react with MMAF or MMAE at a pH of 6.0 to conjugate the drug to the N-terminus of the antibody, thereby preparing an antibody-drug conjugate. In the case of this antibody-drug conjugate, it was shown that the antigen binding activity of the antibody and the cytotoxic efficacy of the drug were maintained even after conjugation of the drug (Examples 3 to 5). In particular, this antibody-drug conjugate showed excellent stability in human serum in vitro compared to another antibody-drug conjugate (comparative conjugate) having a cysteine or lysine bond, and also showed excellent pharmacokinetics in an excellent pharmacokinetic experiment performed using rats (Example 6). In addition, this antibody-drug conjugate showed excellent anticancer activity compared to the comparative conjugate in anticancer animal models, but showed low toxicity similar to a control group in terms of weight, hepatotoxicity, blood and the like (Examples 7 and 8). Furthermore, results similar to the above-described results in terms of antigen binding activity, cytotoxicity and the like were obtained even when other drugs such as MMAE were used or when other antibodies such as Lorvotuzumab, Brentuximab and Glembatumumab were used (Example 9), indicating that the technology according to the present invention, in which a drug is conjugated to the N-terminus of the heavy chain or light chain of an antibody, can become a platform technology in the preparation of antibody-drug conjugates.

In another aspect, the present invention is directed to a method for preparing the antibody-drug conjugate.

The antibody-drug conjugate and its components are as described above.

Specifically, the method for preparing the antibody-drug conjugate comprises allowing an antibody to react with a drug containing a reactive group capable of crosslinking with an α-amine group, thereby conjugating the drug to the N-terminal α-amine group of the heavy chain or light chain of the antibody.

In addition, the method for preparing the antibody-drug conjugate may further comprise separating the antibody-drug conjugate from a reaction product including the antibody and the drug, which did not form the conjugate.

Specifically, in the preparation method, the antibody and the drug may be conjugated to each other at a pH of 4.0-6.5, more specifically 5.5-6.5, even more specifically 6.0. As described above, the present invention has an advantage in that specific conjugation between an aldehyde group present in the drug or its linker and the N-terminal α-amine of the antibody can occur at low pH.

The process of separating the antibody-drug conjugate can be performed by various methods known in that art. For example, it can be performed by a chromatographic process including size exclusion chromatography, but is not specifically limited thereto.

In still another aspect, the present invention is directed to a composition comprising the antibody-drug conjugate.

The composition may be in the form of a pharmaceutical composition for treating cancer or autoimmune disease, which comprise the antibody-drug conjugate. In this case, the antibody may be an antibody that binds specifically to a cancer cell surface antigen or a surface antigen of a tissue in which autoimmune disease has occurred. The pharmaceutical composition of the present invention may further comprise a pharmaceutically acceptable carrier.

The antibody, the drug, the cancer cell surface antigen and the surface antigen of the tissue in which autoimmune disease has occurred are as described above.

As used herein, the term "cancer" includes all the kinds of cancers without limitations, but examples of the cancer may include esophageal cancer, stomach cancer, large intestine cancer, rectal cancer, oral cancer, pharynx cancer, larynx cancer, lung cancer, colon cancer, breast cancer, uterine cervical cancer, endometrial cancer, ovarian cancer, prostate cancer, testis cancer, bladder cancer, renal cancer, liver cancer, pancreatic cancer, bone cancer, connective tissue cancer, skin cancer, brain cancer, thyroid cancer, leukemia, Hodgkin's disease, lymphoma, and multiple myeloid blood cancer. A cancer that can be treated depending on the kind of an antigen specific to the cancer cell surface antigen may be selected.

The term "autoimmune disease", as used herein, refers to any autoimmune disease that is targeted by the antibody-drug conjugate. Examples of the autoimmune disease include rheumatoid arthritis, systemic scleroderma, systemic lupus erythematosus, atomic dermatitis, psoriasis, alopecia areata, asthma, Crohn's disease, Behcet's disease, Sjögren's syndrome, Guillain-Barre syndrome, chronic thyroiditis, multiple sclerosis, polymyositis, ankylsoing spondylitis, fibrositis, and polyarteritis nodosa.

As used herein, the term "pharmaceutically acceptable carrier" refers to a carrier or diluent that does not impair the biological activity and characteristics of an administered compound without irritating an organism. As a pharmaceutically acceptable carrier in a composition that is formulated as a liquid solution, a sterile and biocompatible carrier is used. The pharmaceutically acceptable carrier may be physiological saline, sterile water, Ringer's solution, buffered saline, albumin injection solution, dextrose solution, maltodextrin solution, glycerol, ethanol, or a mixture of two or more thereof. In addition, the composition of the present invention may, if necessary, comprise other conventional additives, including antioxidants, buffers, and bacteriostatic agents.

The carrier is not limited particularly, but for oral administration, the composition of the present invention can comprises binders, lubricants, disintegrants, excipients, emulsifiers, dispersions, stabilizers, suspending agents, pigments, perfumes, etc., for injection administration, the composition of the present invention can comprises buffers, preservatives, analgesics, emulsifiers, isotonic agents, stabilizers, etc., and for local administration, the composition of the present invention can comprises bases, excipients, lubricants, preservatives, etc., can be used.

The inventive composition can be formulated with a pharmaceutically acceptable carrier as described above in various manners. For example, for oral administration, the composition of the present invention can be formulated in the form of tablet, troche, capsule, elixir, suspension, syrup, wafer, etc., and for injection administration, the composition can be formulated as a unit dosage ampoule or a multiple dosage form. The composition can also be formulated as solution, suspension, tablet, pill, capsule, sustained-release formulation, etc.

In the meantime, examples of carrier, excipient or diluent suitable for the formulation of the composition may include lactose, dextrose, sucrose, sorbitol, mannitol, xylitol, erythritol, maltitol, starch, acacia rubber, alginate, gelatin, calcium phosphate, calcium silicate, cellulose, methyl cellulose, microcrystalline cellulose, polyvinylpyrrolidone, water, methylhydroxybenzoate, propylhydroxybenzoate, magnesium stearate and mineral oils. In addition, the composition of the present invention may additionally contain fillers, anti-aggregating agents, lubricants, wetting agents, perfumes, and preservatives.

In addition, the pharmaceutical composition of the present invention may include any one formulation selected from the group consisting of tablets, pills, powders, granules, capsules, suspensions, internal solutions, emulsions, syrups, sterilized aqueous solutions, non-aqueous solvents, suspensions, emulsions, lyophilized agents, and suppositories according to a conventional method.

In addition, the conjugate may be used in a mixture with various pharmaceutically acceptable carriers such as physiological saline or organic solvents. To increase the stability or absorption property of the conjugate, the conjugate may be used in combination with carbohydrates such as glucose, sucrose or dextran, antioxidants such as ascorbic acid or glutathione, chelating agents, low-molecular-weight proteins, or stabilizers.

In yet another aspect, the present invention is directed to a method of treating cancer or autoimmune disease using the antibody-drug conjugate or the composition. The antibody may be an antibody that binds specifically to a cancer cell surface antigen, and the drug may be a drug for treating cancer. In addition, the antibody may be an antibody that binds specifically a surface antigen of a tissue in which autoimmune disease has occurred, and the drug may be a drug for treating autoimmune disease.

The antibody and the drug are as described above.

The method may be a method for treatment of cancer or autoimmune disease, which comprises administering the pharmaceutical composition to a subject in need of the treatment. The antibody-drug conjugate and carriers that are used in the method are as described above.

The composition may be administered as single or multiple doses in a pharmaceutically effective amount. In this case, the composition may be administered in the form of liquid, powder, aerosol, capsule, enteric-coated tablet, or suppository. The composition of the present invention can be administered intraperitoneally, intravenously, intramuscularly, subcutaneously, transdermally, orally, topically, intranasally, intrapulmonarily or intrarectally, but is not limited thereto. However, because the protein antibody is digested when administered orally, the active ingredient in the composition for oral administration should be coated or formulated so as to be protected from degradation in the stomach. In addition, the pharmaceutical composition may be administered by any device by which the active ingredient may be delivered to target cells. Furthermore, the pharmaceutical composition of the present invention may be administered individually or in combination with other therapeutic agents, and may be administered sequentially or simultaneously with conventional therapeutic agents.

The composition comprising the antibody-drug conjugate of the present invention is administered in a pharmaceutically effective amount. As used herein, the term "pharmaceutically effective amount" refers to an amount sufficient to treat or prevent the disease at a reasonable benefit/risk ratio applicable for medical treatment or prevention, and an effective dosage level can be determined according to the severity of disease, the activity of the drug, the patient's age, weight, health conditions, gender, and sensitivity to the drug, time of administration, route of administration and the discharge rate, duration of treatment, combination with the composition of the present invention used, or well-known elements and elements in other medical fields, including drugs used simultaneously.

In a further aspect, the present invention is directed to a method for screening an antibody suitable for use in preparation in the antibody-drug conjugate.

In the preparation of the antibody-drug conjugate according to the present invention, an antibody suitable for use in effectively preparing the antibody-drug conjugate by conjugating a drug to the N-terminus (particularly α-amine) of the antibody can be screened and selected.

EXAMPLES

Hereinafter, the present invention will be described in further detail with reference to examples. It will be obvious to a person having ordinary skill in the art that these examples are illustrative purposes only and are not to be construed to limit the scope of the present invention. Thus, the substantial scope of the present invention will be defined by the appended claims and equivalents thereof.

Example 1: Selection of Model Antibodies

In the preparation of an antibody-cytotoxin conjugate representative of the antibody-drug conjugate of the present invention, the anti-HER2 antibody Trastuzumab, the anti-CD56 antibody Lorvotuzumab, the anti-CD30 antibody Brentuximab and the anti-GPNMB (glycoprotein NMB) antibody Glembatumumab were used as model antibodies in order to examine whether cytotoxin having a linker would be site-selectively conjugated to the antibodies.

The above antibodies were constructed into expression vectors using known amino acid sequence information, and a stable cell line was constructed from the CHO cell line. Alternatively, the antibodies were expressed transiently, incubated and purified.

Example 2: Synthesis of Toxin

Figure 1:
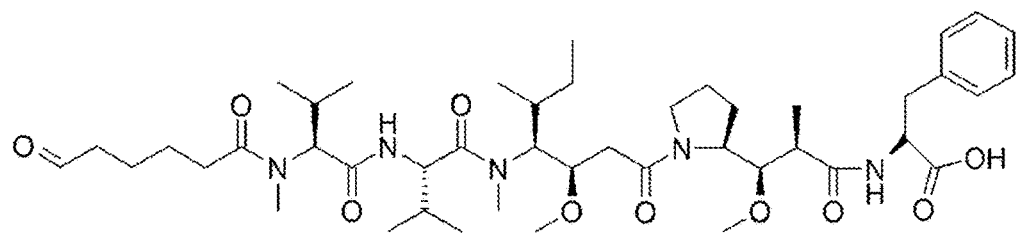
FIG. 1 shows the structural formula of toxin monomethyl auristatin F (MMAF) having an aldehyde linker connected to the end.

Monomethyl auristatin F (MMAF) toxin having an aldehyde linker connected to the end was synthesized (LegoChem Biosciences or XcessBioscience) (FIG. 1). In addition, in order to examine whether the N-terminal conjugation method of the present invention can also be applied to toxins other than MMAF, Monomethyl auristatin E (MMAE) was synthesized (XcessBioscience, USA).

Example 3: Preparation of Monoclonal Antibody-Cytotoxin Conjugate 3-1: Preparation of Monoclonal Antibody-Drug Conjugate According to the Present Invention An antibody was diluted in 100 mM potassium phosphate buffer (pH 5.49) and concentrated to about 7.1 mg/ml. Next, MMAF (LegoChem Biosciences, Korea) connected with a linker having an aldehyde reactive group was dissolved in 50% DMSO (dimethyl sulfoxide) solvent to a concentration of 2.5 mg/ml. Thereafter, the prepared antibody solution and MMAF solution were mixed with each other so as to achieve the following conditions: final 70 mM potassium phosphate (pH 6.0); antibody concentration: 5.0 mg/ml; 14% DMSO; MMAF concentration: 0.3 mg/ml; and the molar ratio between the α-amine of the antibody and MMAF: about 1:2.3 (or the molar ratio between the antibody and MMAF is 1:9). NaCNBH$_3$ (Sigma, USA) was added to the reaction solution to a final concentration of 20 mM, and then reacted at 4° C. for 12 hours with gentle stirring. To separate unreacted antibody and unreacted MMAF connected with the linker, a Sephadex G-25 column (GE Healthcare, USA) or a resource phenyl column (Resource Phe, GE Healthcare, USA) was used. According to this process, a conjugate was prepared in which about three MMAF toxin molecules per antibody molecule were selectively conjugated to the amino terminus of the antibody (FIG. 2).

3-2: Preparation of Control Antibody-Drug Conjugate

According to a conventional technology, a control antibody-drug conjugate was prepared by cysteine conjugation (Thiomab (HC-A114C)+Mal-C6-MMAF), thiol conjugation (Mal-C6-MMAF) or lysine conjugation (SMCC linker, SH-C6-MMAF).

To prepare a thiol-conjugated antibody, an antibody was reduced with TCEP at a pH of 8.0, and then Mal-C4-MMAF was added thereto and allowed to react at 0° C. for 3 hours. After the reaction, thiol was added to the reaction product which was then further reacted. After termination of the reaction, replacement with 1×PBS using a G25 desalting column (GE healthcare, USA) was performed to complete the reaction.

To prepare a cysteine-conjugated antibody, cysteine in a purified antibody was activated, and then Mal-C6-MMAF was added thereto, and conjugation was performed according to a process similar to that used in the preparation of the thiol-conjugated antibody.

A conjugate comprising a lysine-conjugated antibody was prepared with reference to International Patent Publication No. WO2005037992 (Immunogen). First, an antibody was reacted with an SMCC linker, and unreacted SMCC was removed by buffer exchange. The antibody-SMCC conjugate was reacted with SH-C4-MMAF (Concortis bioscience, USA) containing a thiol group, thereby preparing an antibody-SMCC-MMAF conjugate.

The antibody-cytotoxin conjugates prepared by α-amine conjugation according to the present invention are summarized in Table 1 below.

TABLE 1

Antibody-drug conjugates

| Conjugation type | Conjugation conditions | Conjugate name (when Trastuzumab and MMAF are used) |
|---|---|---|
| Cys conjugation | Thiomab (HC A114C), Mal-C6-MMAF | Thiomab-MMAF |
| Thiol conjugation | Mal-C6-MMAF | T-C-MMAF |
| Lys conjugation | SMCC linker, SH-C6-MMAF | T-K-MMAF |
| Amine conjugation | ALD-C6-MMAF (weakly acidic pH) | T-N-MMAF |

The four conjugates prepared as described above were analyzed to determine the DAR (drug antibody ratio) and the site of conjugation. The analysis was performed by LC-MS and peptide mapping.

Example 4: Physicochemical Properties and Biological Properties 4-1: Analysis of Molecular Weight The molecular weights of the antibody-drug conjugates (T-N-MMAF) were determined by LC-MS analysis. The theoretical molecular weight of the drug (MMAF) used is 824.54 Da, and the molecular weight of Trastuzumab is 145 kDa. Thus, the conjugation of the drug to the antibody and the number of drug moieties conjugated to one antibody molecule could be simultaneously determined by mass spectrometry.

To determine the DAR of T-N-MMAF prepared in Example 3, the molecular weight of T-N-MMAF was analyzed by LC/MS. The prepared sample was treated with PNGaseF to remove sugar chains, and then separated through an ACQUITY UPLC BEH 200 SEC column, after which the sample was injected into the Waters Synapt G2-S system to analyze the mass. The results of the analysis are shown in FIG. 3.

Figure 3:
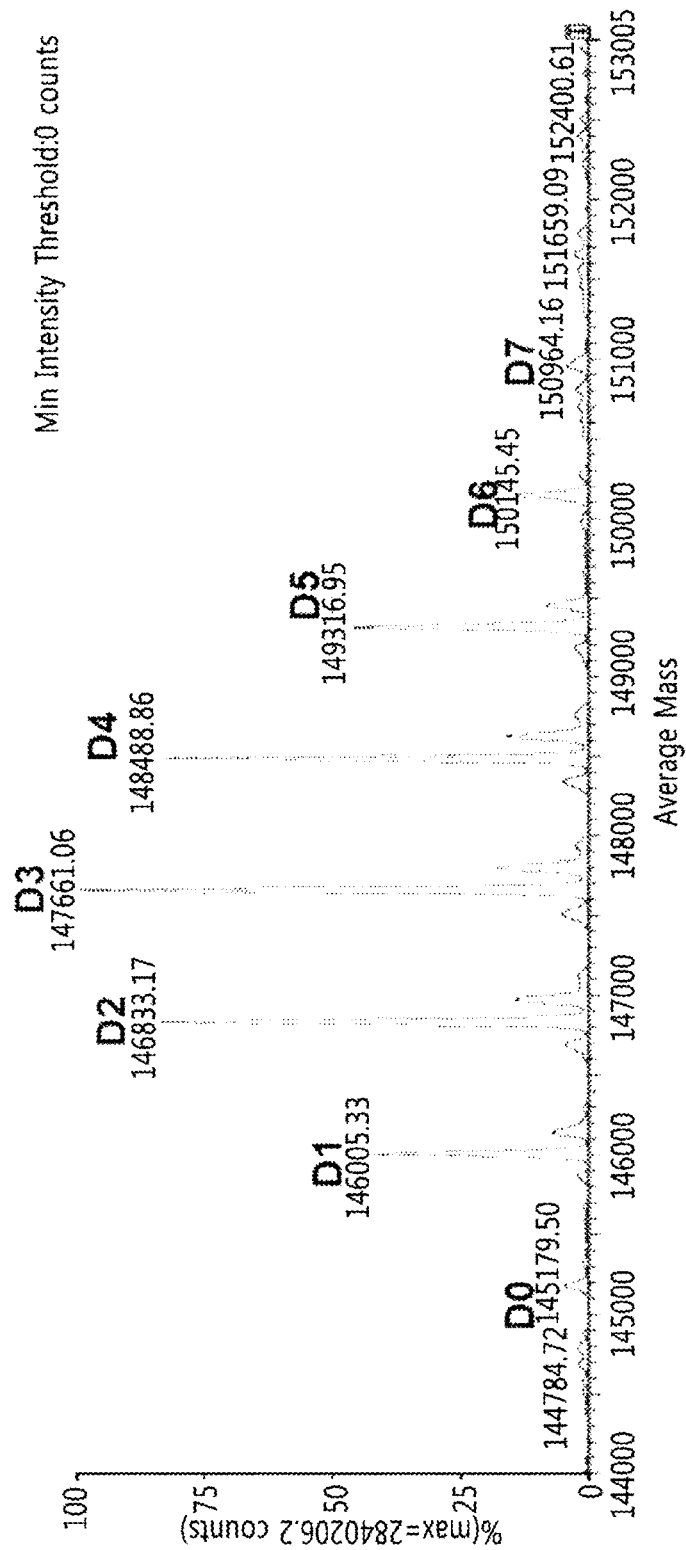
FIG. 3 shows the LC/MS profile of T-N-MMAF.

As a result, as shown in FIG. 3, chemical species ranging from a chemical species (D0) having no drug moiety conjugated thereto to a chemical species (D7) having 7 drug moieties conjugated thereto were detected, and the number of drug moieties conjugated was determined based on whether the difference in molecular weight between peaks was consistent with or similar to the molecular weight of the drug. The relative intensities of the drug moieties are shown in Table 2 below. The DAR was calculated as the weighted average of the chemical species and was DAR=3.2.

TABLE 2

| No. of bound drug | Mass (Da) | Relative intensity (%) | Da |
|---|---|---|---|
| 0 | 145179.5 | 1.8 | — |
| 1 | 146005.3 | 10.7 | 825.8 |
| 2 | 146833.2 | 21.2 | 827.9 |
| 3 | 147661.1 | 25.4 | 827.9 |
| 4 | 148488.9 | 21.0 | 827.8 |
| 5 | 149317.0 | 12.5 | 828.1 |
| 6 | 150145.5 | 5.0 | 828.5 |
| 7 | 150964.2 | 2.3 | 818.7 |
| DAR | | 3.219 | |

DAR = Sum (Intensity (%) × No. of Drug/100)
Drug moiety mass: 828 Da 4-2: Site of Conjugation of Drug The site of conjugation of the drug in the prepared T-N_MMAF conjugates was determined by peptide mapping. T-N-MMAF ADC (having a DAR of 3.2) prepared in Example 3 was treated with Rapigest (Waters), and then treated with trypsin (Roche) to make fragments. The reaction product was separated through an ACQUITY UPLC PST (BEH) C18 column, and the separated peaks were subjected to mass spectrometry through the Waters Synapt G2-S Q/TOF system to determine the sequence of the reaction product. The results of the analysis are shown in FIG. 4.

Figure 4:
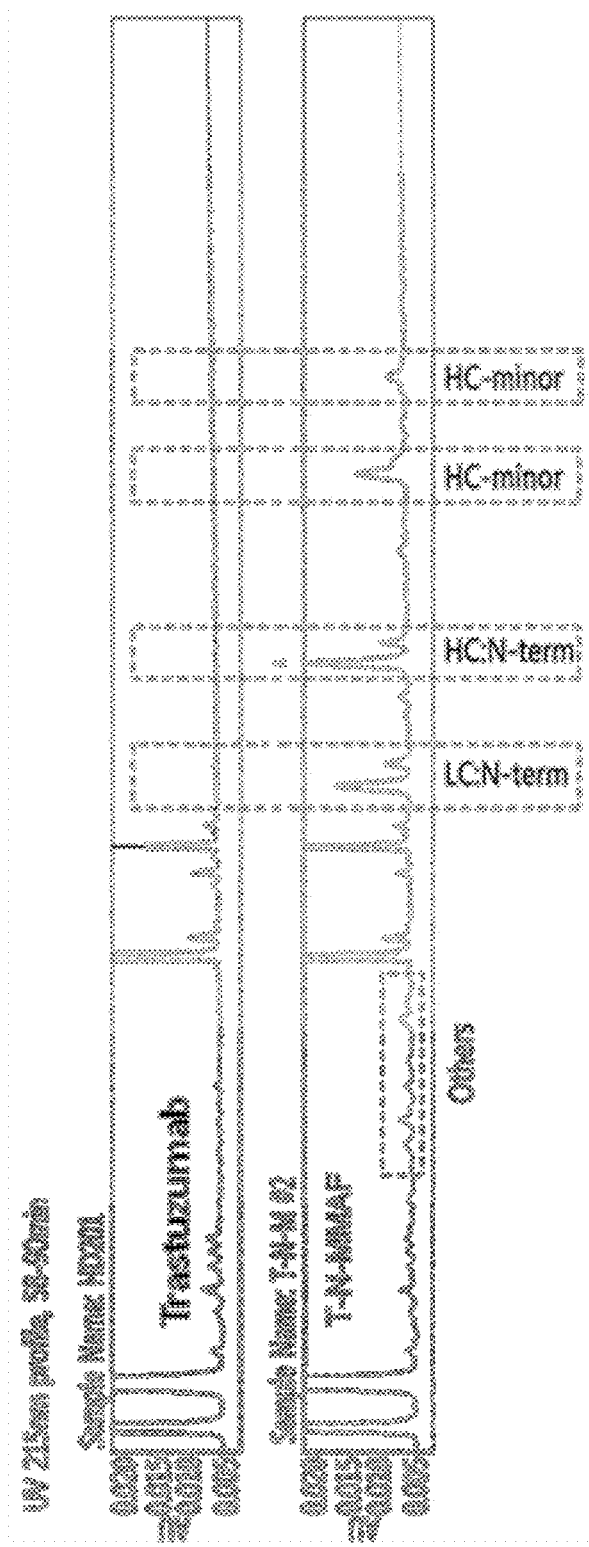
FIG. 4 shows the results of peptide mapping performed to determine the site of binding of a drug in a prepared Trastuzumab-N-MMAF (T-N-MMAF conjugate).

As a result, as shown in FIG. 4, peaks which were not found in the non-conjugated parent antibody were detected in the chromatogram. The results of mass spectrometry indicated that the fragments were the N-terminus of the heavy chain, the N-terminus of the light chain, a portion of the heavy chain, and other small fragments. The ratios of the fragments are shown in Table 3 below. Thus, it can be seen that 75% of the drug was conjugated to the N-terminus and 92% of the drug was selectively conjugated to the N-terminus and the heavy-chain CH2 region, which can be clearly defined.

TABLE 3

| | Trypsin fragment | Ratio |
|---|---|---|
| Heavy chain-N-terminus | EVQLVESGGGLVQPGGSLR (SEQ ID NO: 1) | 46% |

TABLE 3-continued

| | Trypsin fragment | Ratio |
|---|---|---|
| Light chain-N-terminus | DIQMTQSPSSLSASVGDR (SEQ ID NO: 2) | 29% |
| Heavy chain-CH2 | THTCPPCPAPELLGGPSVFLFPP KPKDTLMISR (SEQ ID NO: 3) | 17% |
| Others | — | 8% |

4-3: Analysis of Purity

To determine the aggregate content of the prepared T-N-MMAF conjugate, purity analysis of the conjugate was performed by SE-HPLC and SDS-PAGE analysis. Size exclusion chromatography was used in a TSK-Gel3000SWXL column using PBS as a mobile phase, and SDS-PAGE was performed using 4-12% Novex NuPAGE gel. The results of the chromatography are shown in FIG. 5.

Figure 5:
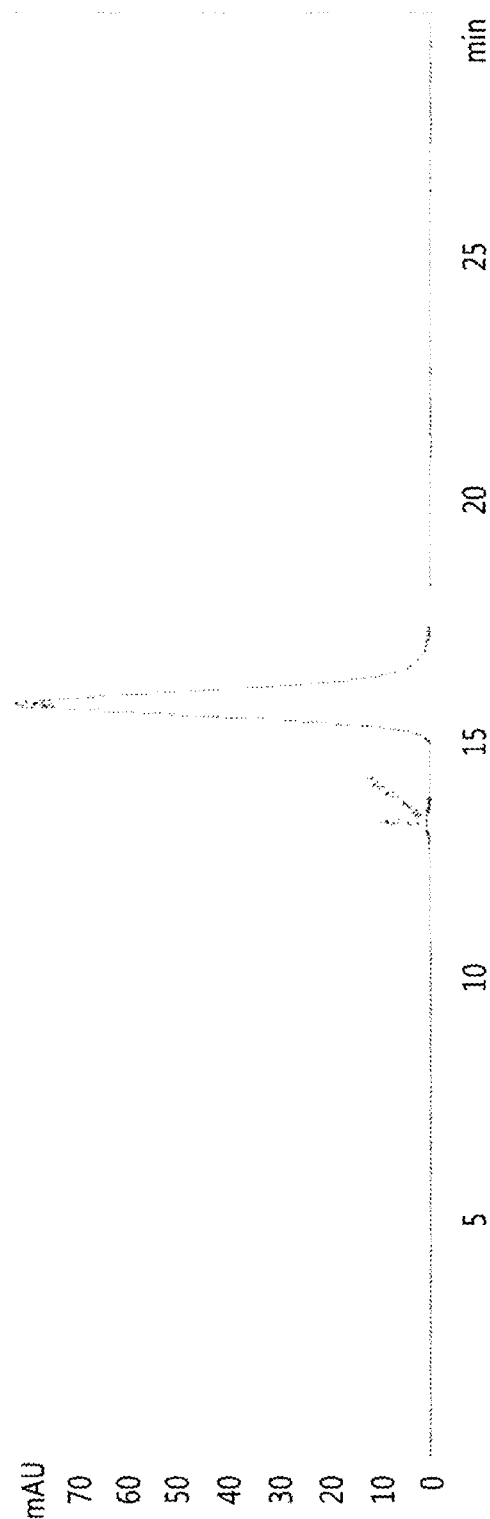
FIG. 5 shows the results of SEC-HPLC analysis of a prepared T-N-MMAF.

As a result, as shown in FIG. 5, the purity of the monomer was 98.8%, which is suitable for an efficacy test, and fragmentation or cross-linking was not detected.

4-4: Antigen Binding Activity

In order to examine the antigen binding activity of the antibody is maintained even after the drug was conjugated thereto, the antigen binding activity of the drug-conjugated antibody was measured by a method of measuring surface plasmon resonance using Biacore™. As a control antibody, a natural antibody was used. The antigen (ErbB2) binding activity was analyzed using Biacore T200, and each antibody was immobilized on a CM5 sensor chip (GE healthcare, USA) using an amine coupling kit, after which kD (M) was calculated by measuring and analyzing on/off rate while injecting ErbB2 at concentrations of 50, 16.67, 5.56, 1.85, 0.62 and 0.21 nM and at a rate of 30 uL/min.

TABLE 4

| | Antigen binding activity | | |
|---|---|---|---|
| Samples | Test 1 ($10^{-10}$ M) | Test 2 ($10^{-10}$ M) | Average ($10^{-10}$ M) |
| Trastuzumab | 1.3 | 2.2 | 1.8 |
| T-N-MMAF (DAR 1.6) | 1.2 | 0.9 | 1.1 |
| T-N-MMAF (DAR 3.2) | 1.1 | 0.7 | 0.9 |

As a result, as summarized in Table 4 above, it was found that an antigen binding activity of about 0.1 nM similar to that of the natural antibody was maintained even after drug conjugation regardless of the DAR.

Example 5: In Vitro Cytotoxicity Analysis

In order to examine the in vitro efficacy of the prepared antibody-cytotoxin conjugate, an anti-proliferation assay was performed using BT474, HCC1954, SKOV-3, JIMT-1 cell lines which are HER2-expressing tumor cell lines. Each of the cell lines was cultured and suspended at a concentration of $1 \times 10^5$ cells/ml, and 100 μl of the suspension was loaded into each well of a 96-well plate. The cells were incubated in an incubator for 3 hours, and then 100 μl of the antibody-cytotoxin conjugate diluted to various concentrations was added to each well of the plate and incubated in an incubator for 4 days. A 1:10 dilution of CCK-8 (Dojindo) was added to each well of the plate, which was then covered with a foil and incubated in an incubator for 2-5 hours. Next, the absorbance of each well at 450 nm was measured using a SpectraMax 190 microplate reader (Molecular Device).

TABLE 5

| | Cytotoxicity ($IC_{50}$ (pM)) | | |
|---|---|---|---|
| Cell line | T-N-MMAF (DAR 3.2) | T-C-MMAF (DAR 3.6) | T-K-MMAF (DAR 3.9) |
| HCC1954 | 40 | 22 | 45 |
| SKOV-3 | 104 | 59 | N.D. |
| JIMT1 | 253 | 98 | 727 |
| BT474 | 116 | 49 | 77 |

As a result, as shown in Table 5 below, T-N-MMAF showed cytotoxicity slightly lower than T-C-MMAF in all the four cancer cell lines, but a significant decrease in cytotoxicity, which can influence in vivo efficacy, was not observed.

Example 6: Stability Test 6-1: Stability in Human Serum In Vitro

Using T-N-MMAF prepared in Example 3 and control antibodies, including a natural antibody, T-C-MMAF and Thiomab-MMAF, a stability test in human serum in vitro was performed. The antibody-cytotoxin conjugate was buffer-exchanged with 1×PBS and concentrated to 3.33 mg/ml, and then mixed with human serum (Sigma, USA) at a ratio of 1:9 (v/v) and allowed to stand at 37° C. for 7 days. After 7 days, to remove proteins other the stored sample was treated with MabSelectSure (GE healthcare, USA) than the antibody-cytotoxin conjugate contained in the sample in order to minimize interference in LC/MS analysis. The stability of the conjugate in human serum in vitro was analyzed by LC/MS, and the results of the analysis are shown in Table 6 below.

TABLE 6

| Samples | Relative content of monoclonal antibody (7 days of storage, %) | Relative content of conjugate (7 days of storage, %) | Relative content of DAR (7 days of storage, %) |
|---|---|---|---|
| Trastuzumab | 90.0 | — | — |
| T-N-MMAF | 89.3 | 90.5 | 101.4 |
| T-C-MMAF | 49.2 | 32.3 | 65.6 |
| Thiomab-MMAF | 69.9 | 59.5 | 85.1 |

As a result, as can be seen in Table 6 above, the changes in the content and DAR of T-N-MMAF compared to the control natural antibody after 7 days of storage were not observed. However, in the case of T-C-MMAF and Thiomab-MMAF, which are the comparative antibody-drug conjugates, decreases in the total antibody content and the DAR could be observed.

6-2: Rat Pharmacokinetics (PK)

In vivo stability was compared and analyzed through a rat pharmacokinetic experiment. Each of three ADCs (T-K-MMAF, T-C-MMAF, and T-N-MMAF) and Trastuzumab were injected intravenously once to female Sprague-Dawley rats at a dose of 2.5 mg/kg. At 0.05, 0.5, 1, 6, 24, 72, 168, 240 and 336 hours after administration of the substances, blood was collected. A total antibody assay of analyzing all antibodies binding to ErbB2 in blood and a conjugated antibody assay of analyzing an antibody maintaining drug conjugation were performed by an ELISA method.

The total antibody content was analyzed by an ELISA method as follows.

A 96-well microplate was coated with ErbB2 (R&D systems), and then a sample was added to the plate and incubated at a temperature of 37° C. for 1 hour. The plate was washed with PBST to remove all non-fixed substances, and then the absorbance of the plate at 450 nm was measured using HRP-conjugated anti-human kappa light chain antibody and 3,3',5,5'-tetramethylbenzidine (TMB, Sigma, 10440), thereby determining the total antibody content of the sample.

Figure 6:
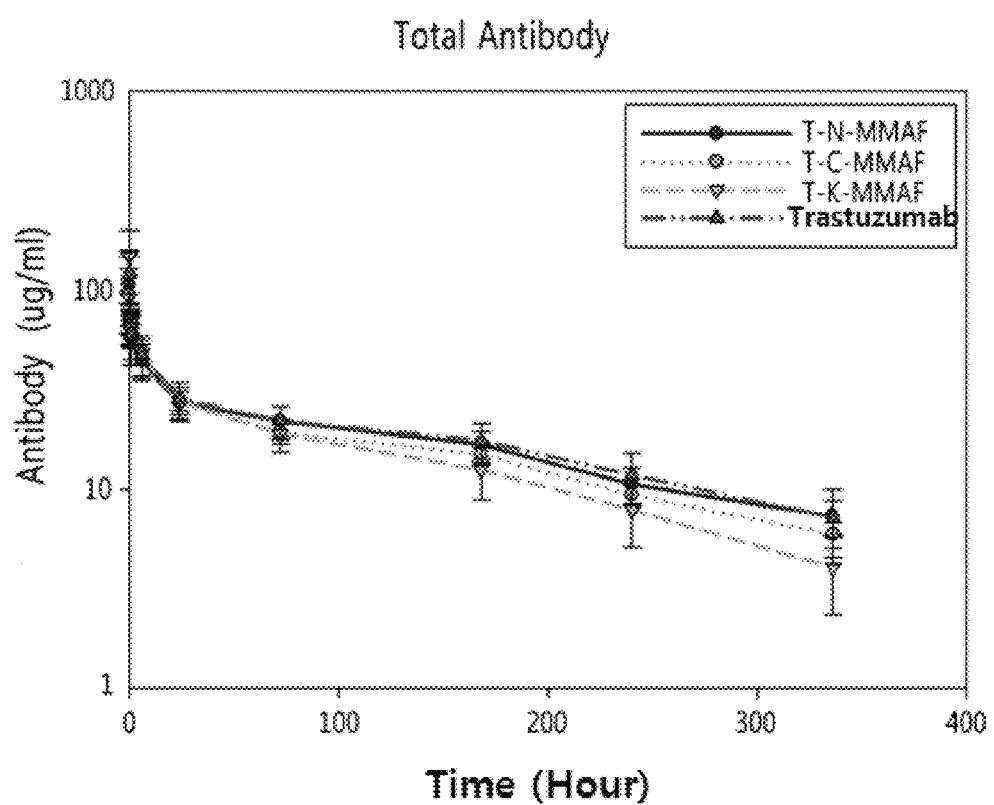
FIG. 6 shows a time-dependent change in the blood concentration of total antibody in rats.
Figure 7:
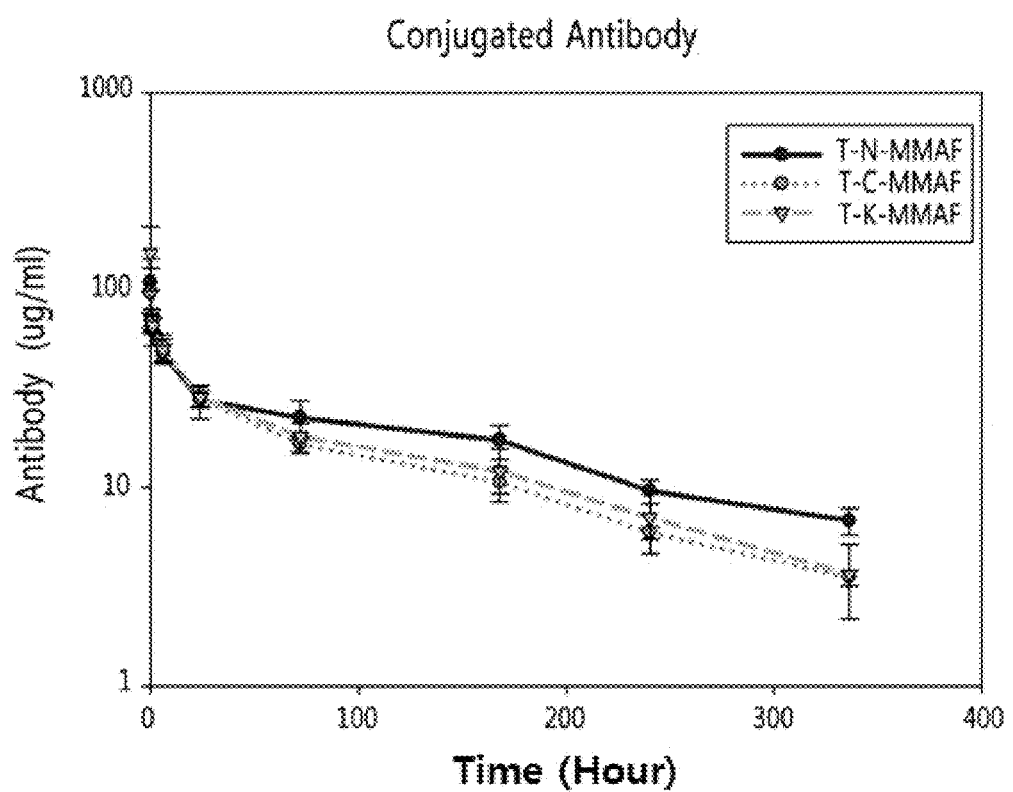
FIG. 7 shows a time-dependent change in the blood concentration of conjugated antibody.
Figure 8:
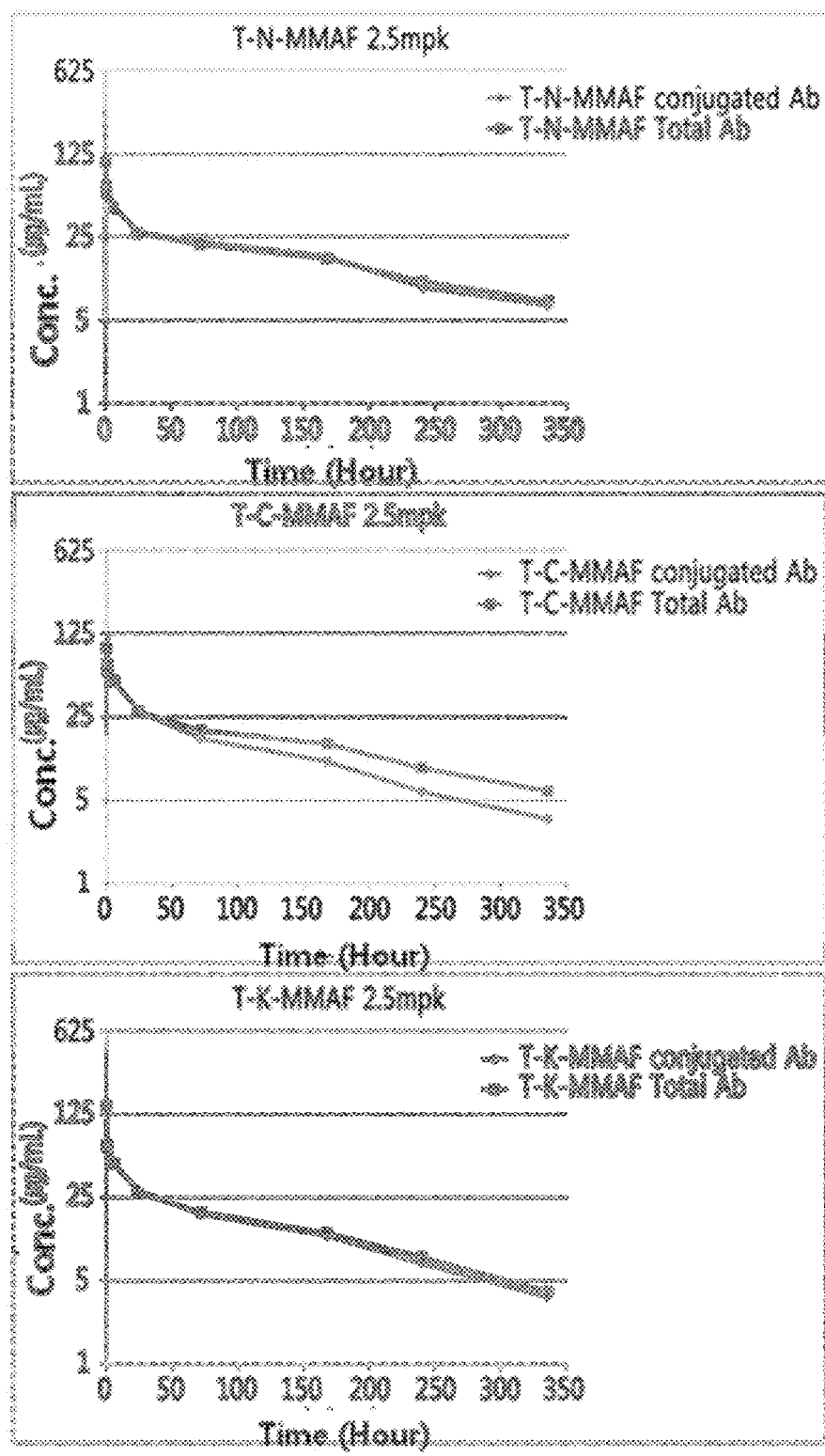
FIG. 8 shows a comparison of the PK profiles of total antibody and conjugated antibody between antibody-drug conjugates (ADCs).

The conjugated antibody assay was performed by a method similar to the above-described method. Specifically, a 96-well microplate was coated with anti-MMAF antibody (Young In Frontier), and then a sample was added to the plate and incubated at a temperature of 37° C. for 1 hour. Next, biotinylated ErbB2 (ACROBIOSYSTEMS, USA), streptavidin-HRP and TMB were sequentially added to the plate to develop color, and then the absorbance of the plate at 450 nm was measured to determine the concentration of the conjugated antibody. The results of the measurement are shown in FIGS. 6 to 8 and Table 7 below.

TABLE 7

PK parameters measured after administering ADCs to rats at a dose of 2.5 mg/kg

| Treatment (n = 5, each) 2-compartment modeling | Total Ab | | | Conjugated Ab | | |
|---|---|---|---|---|---|---|
| | AUC (hr * µg/ml) | $T_{1/2}$ (hr) | $C_{max}$ (µg/ml) | AUC (hr * µg/ml) | $T_{1/2}$ (hr) | $C_{max}$ (µg/ml) |
| Trastuzumab | 6964.9 | 115.7 | 128.1 | — | — | — |
| T-N-MMAF | 6795.7 | 122.1 | 111.2 | 6813.2 | 118.3 | 112.4 |
| T-C-MMAF | 5933.5 | 111.6 | 94.3 | 4315.4 | 84.6 | 93.7 |
| T-K-MMAF | 4324.3 | 65.1 | 157.5 | 3781.7 | 53.2 | 190.0 |

Example 7: Test for Anticancer Effect in Anticancer Model Animals

In order to examine the efficacy of three ADCs prepared by different techniques and the difference in efficacy by drug-antibody ratio (DAR), an in vivo efficacy test was performed in breast cancer (HCC 1954) xenograft models using nude rats.

Each of four ADCs, that is, T-N-M (DAR: about 1.6 and 3.2), T-C-M (DAR: about 3.7) and T-K-M (DAR: about 3.9), was administered intravenously once to HCC1954 cell-transplanted rats at a dose of 1 mg/kg, and then the degree of inhibition of growth of the transplanted tumor was compared between the test groups. The results are shown in FIGS. 9 and 10.

Figure 9:
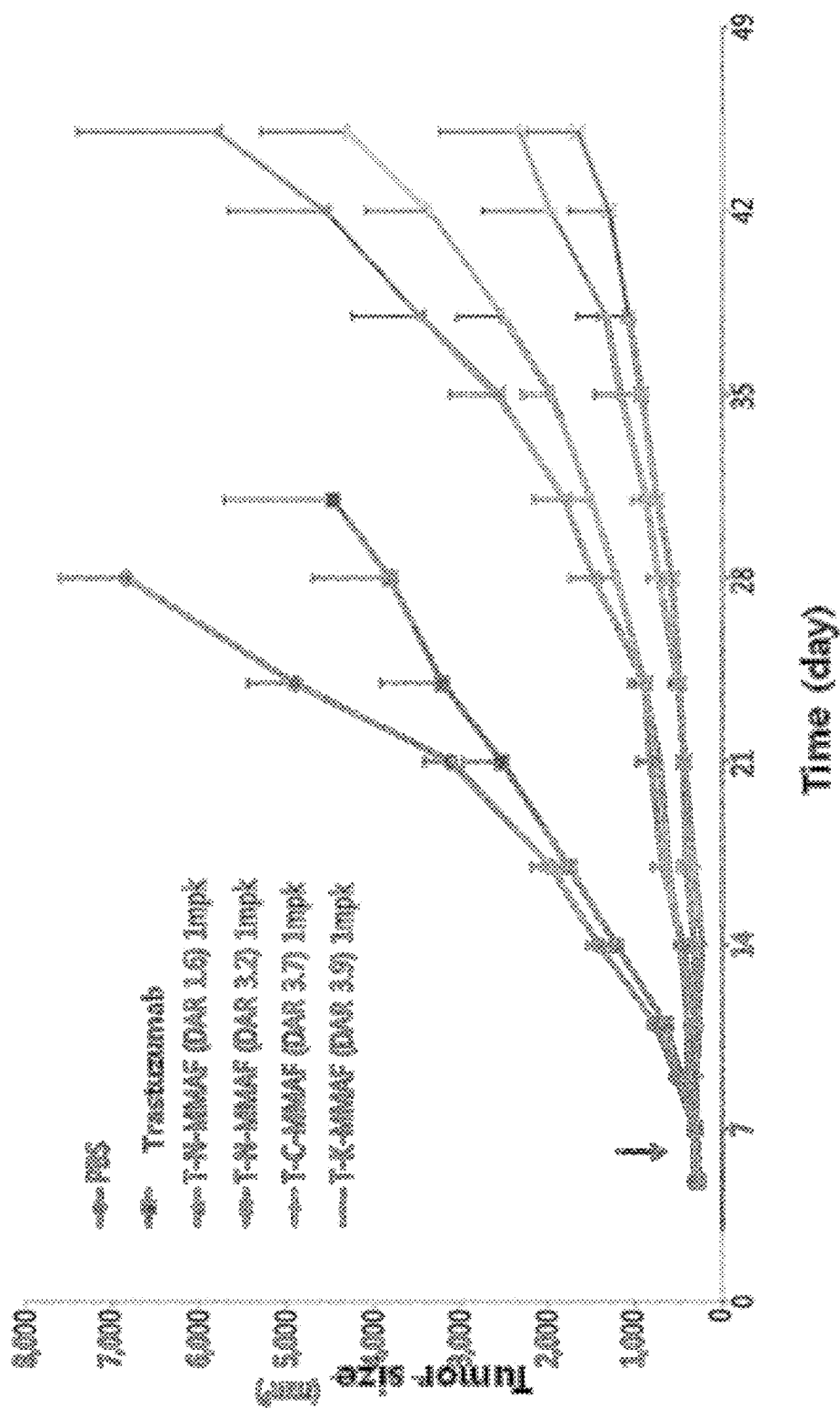
FIG. 9 shows growth curves of tumors formed by the HCC1954 cell line in nude rat xenograft models.
Figure 10:
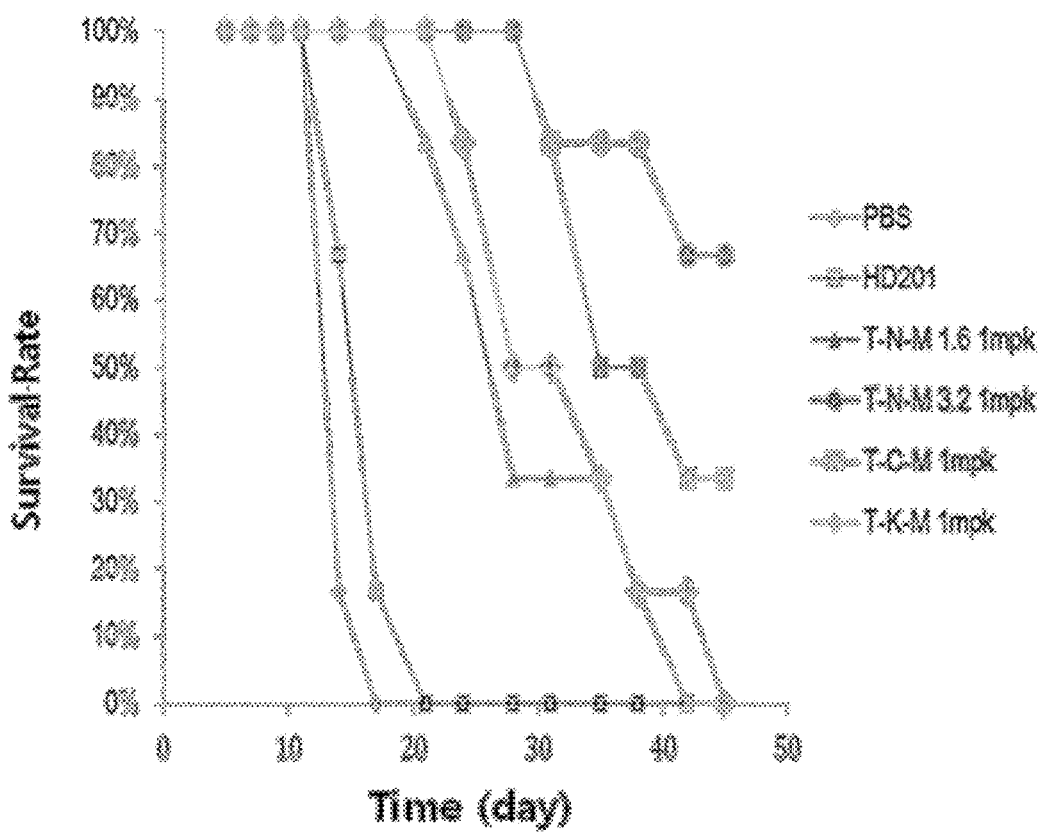
FIG. 10 shows survival curves obtained in nude rat xenograft model experiments performed to measure the tumor volume at the endpoint.

As a result, as shown in FIGS. 9 and 10, the antibody according to the present invention had an excellent anticancer effect compared to the control and comparative antibodies.

Example 8: Toxicity Test

In order to examine whether stability varying depending on the technique for preparation of ADCs influences toxicity, a single-dose toxicity test was performed using SD rats. Each of three ADCs was administered intravenously once at a high dose of 200 mpk. As comparative groups, an antibody alone and MMAF were administered at a dose of 200 mpk. The weight was measured everyday during a period ranging from the time point of administration of the test substance to the end of the test (day 12). Biochemical analysis of the blood was performed at 5 days after administration. Measurement items were AST and ALT for determining hepatotoxicity and typical hematological toxicity, neutrophils and platelets.

8-1: Change in Weight

Figure 11:
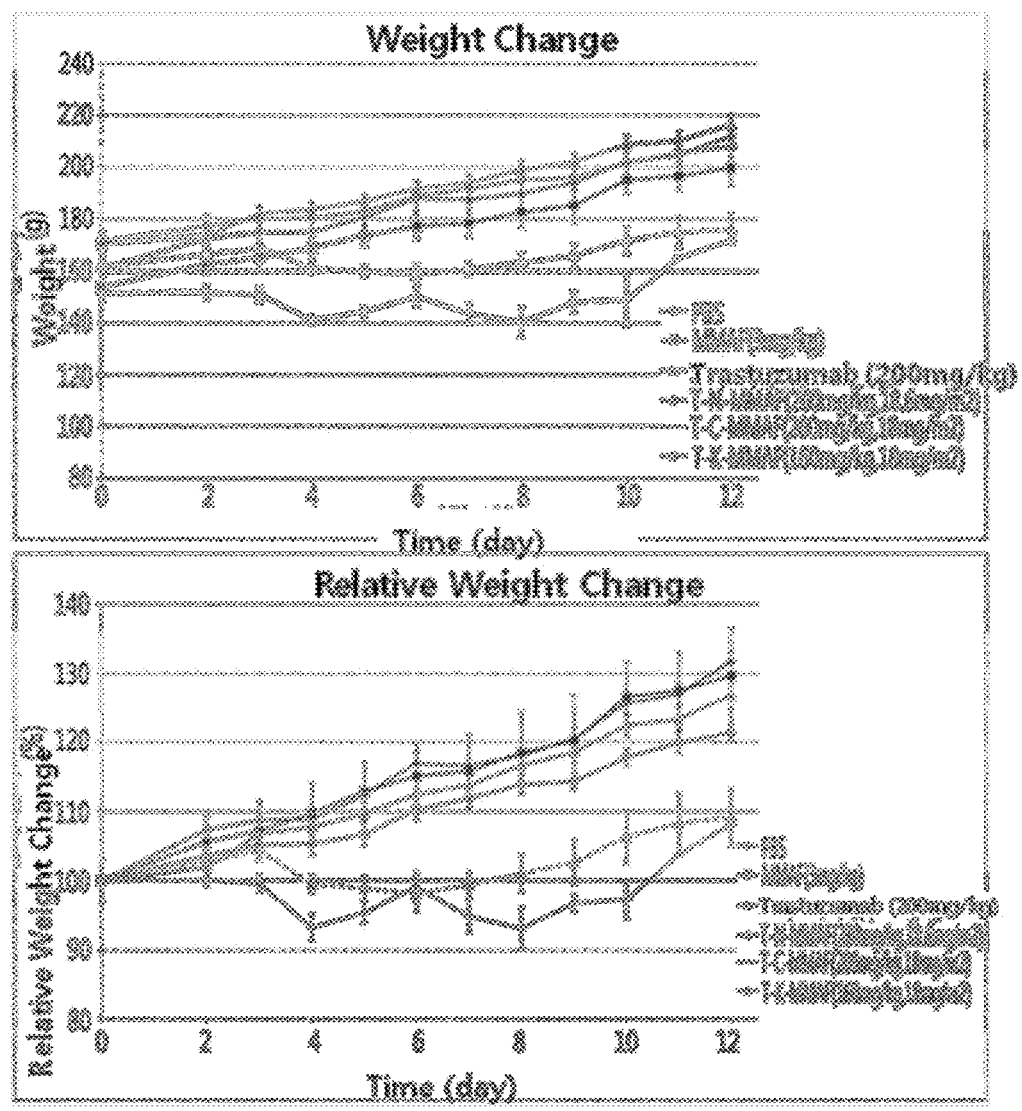
FIG. 11 shows the change and relative change in weight by administration of each antibody-drug conjugate (ADC).

The results of measurement of changes in the weight are shown in FIG. 11. As shown in FIG. 11, the T-C-MMAF and T-K-MMAF groups showed a distinct decrease in the weight compared to the T-N-MMAF group and other groups. In particular, in the case of the group administered with T-C-MMAF, all animals excluding one animal did die after day 8.

8-2: Biochemical Analysis (Hepatotoxicity)

In order to examine whether the ADCs cause hepatotoxicity, biochemical analysis of blood collected at day 5 after administration of the ADCs was performed. The analysis was performed using the Au480 clinical analyzer (Beckman Coulter, USA), and the levels of AST (aspartate aminotransferase) and ALT (alanine aminotransferase) indicative of hepatotoxicity were measured. The results of the measurement are shown in FIG. 12.

Figure 12:
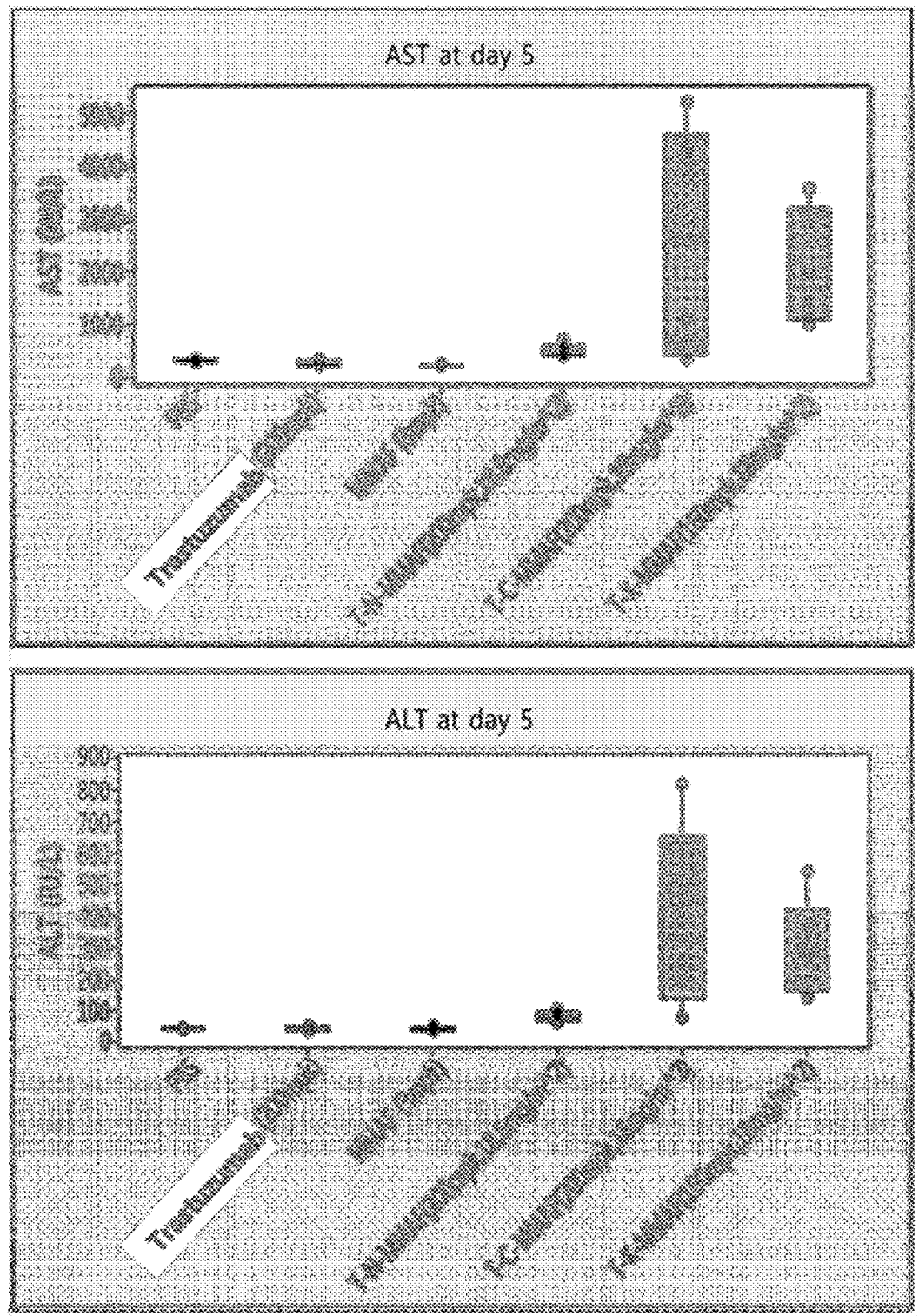
FIG. 12 shows the results of examining whether the administration of each ADC caused hepatotoxicity.

As a result, as shown in FIG. 12, it could be observed that the T-N-MMAF group according to the present invention showed no significant difference from other control groups including PBS, indicating that it did not caused abrupt or serious hepatotoxicity. However, a significant increase in AST and ALT was observed in the T-C-MMAF and T-K-MMAF groups, indicating that administration of the drugs caused hepatotoxicity.

8-3: Hematological Analysis (Neutropenia and Thrombocytopenia)

Because the major clinical toxicities of currently approved ADCs indicate the hematological properties, hematological analysis of blood collected at day 5 after administration of the ADCs was performed using the Hemavet 950 FS hematological analyzer (Drew Scientific Inc., USA). The results of the analyzer are shown in FIG. 13.

Figure 13:
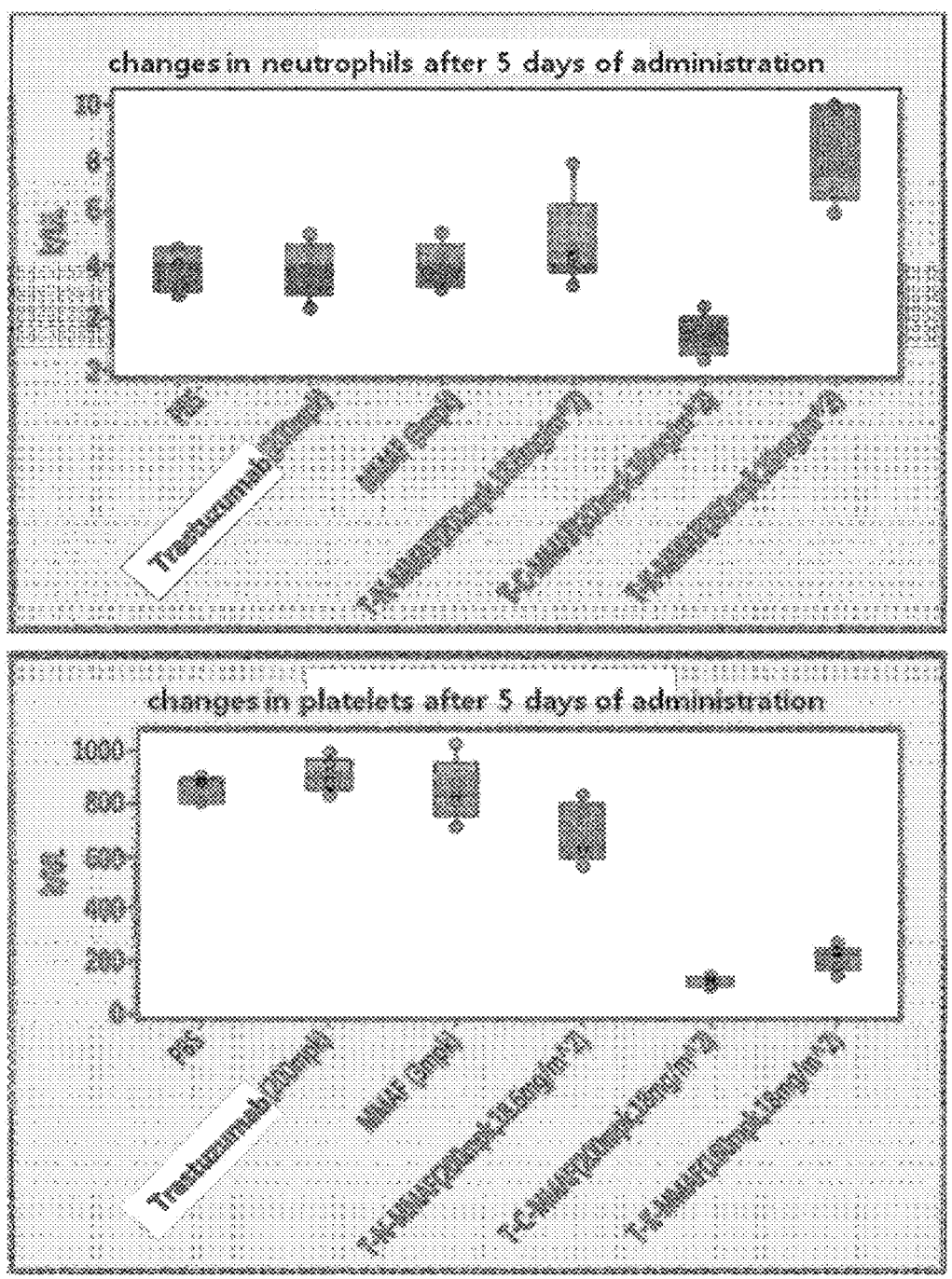
FIG. 13 shows the changes in neutrophils and platelets by administration of each ADC.

As a result, as shown in FIG. 13, the T-N-MMAF group showed no significant change in the number of neutrophils compared to the control groups including PBS, suggesting that T-N-MMAF did not cause abrupt and serious hematological toxicity. However, the T-C-MMAF group showed a significant decrease in the number of neutrophils, and the T-K-MMAF group showed a significant increase in the number of neutrophils, which decreased immediately after administration and then increased. Thus, for these two groups, it could be concluded that abrupt hematological toxicity was caused by administration of the drugs.

The number of platelets was noticeably smaller than in the T-N-MMAF group than in other control groups including PBS. However, the T-C-MMAF and T-K-MMAF groups showed a significant decrease in the number of platelets, indicating that abrupt toxicity was caused by administration of the drugs.

Example 9: Examination of Platform Function

Whether the method for preparing the antibody-drug conjugate according to the present invention can be applied to various antibody-drug conjugates was examined. For this, the method was applied to various drugs or antibodies and various antibody forms in order to examine the function thereof.

9-1: Examination of Function According to Type of Drug

In order to determine whether the method for preparing the antibody-drug conjugate according to the present invention can be applied to various drugs, N-terminal conjugation of various drugs was performed using Trastuzumab as a model antibody. Specifically, two drugs (MMAF and MMAE) were used, and the results obtained using MMAF are as described in the Examples above. Antibody-drug conjugates were prepared according to the method described in Example 1, and the DAR analysis, in vitro stability and rat PK of the prepared antibody-drug conjugates were performed according to the methods described in the Examples above.

9-1-1: Preparation of T-N-MMAE

Figure 14:
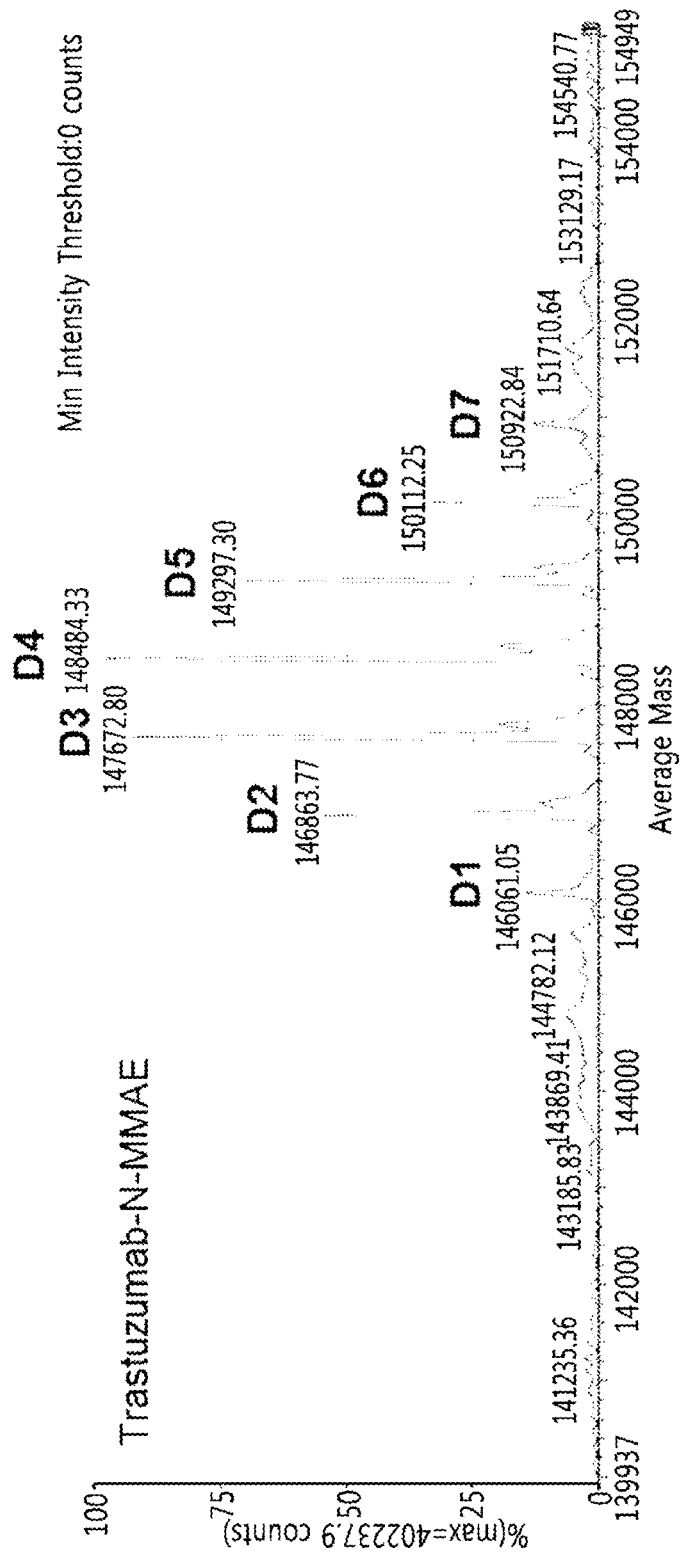
FIG. 14 shows the results of LC/MS analysis of T-N-MMAE.

According to a conjugate between MMAE (XcessBioscience, USA) and an antibody was prepared. To determine the DAR of the conjugate, the molecular weight of the conjugate was analyzed by LC/MS, and the results of the analysis are shown in FIG. 14 and Table 8 below.

TABLE 8

Chemical species distribution by DAR of T-N-MMAE and average DAR

| No. of drug | Mass (Da) | Relative content (%) | Delta mass |
|---|---|---|---|
| D0 | N/D | N/D | |
| D1 | 146061.05 | 6.3 | |
| D2 | 146863.77 | 14.3 | 802.72 |
| D3 | 147672.80 | 23.3 | 809.03 |
| D4 | 148484.33 | 24.2 | 811.53 |
| D5 | 149297.30 | 16.5 | 812.97 |
| D6 | 150112.25 | 8.6 | 814.95 |
| D7 | 150922.84 | 6.8 | 810.59 |
| DAR | | 3.83 | |

9-1-2: Analysis of Stability of T-N-MMAE in Human Serum

According to the method of Example 6, the stability of T-N-MMAE ADC in serum was evaluated. The concentration of ADC in each sample was measured by the total antibody assay using ELISA, and a change in the DAR was measured by LC/MS.

TABLE 9

| | μg/ml | % | DAR | % |
|---|---|---|---|---|
| Day 0 | 364.8 | 100% | 3.17 | 100% |
| Day 3 | 346.9 | 95% | 3.33 | 105% |
| Day 7 | 294.8 | 81% | 3.28 | 103% |

9-1-3: Rat PK of T-N-MMAE

In order to evaluate the in vivo stability of the prepared MMAE conjugate, a PK study in SD rats was performed according to a method similar to that of Example 6. Shortly, 2.5 mg/pk of the ADC was administered to female SD rats. At 12 min, 30 min, 1 hour, 6 hour, 24 hours, 3 days, 7 days, 10 days, 14 days, 17 days and 21 days after administration of the ADC, blood was collected from the rats, and the concentrations of total protein and conjugated antibody in the blood were measured according to the above-described methods using an ELISA technique.

TABLE 10

Rat PK parameters of T-N-MMAE

| Group | AUC (hr*μg/ml) | Conjugate/ Total ratio | half-life (hr) | Conjugate/ Total ratio |
|---|---|---|---|---|
| trastuzumab | 5868.83 | | 169.6 | |
| T-N-MMAF (T) | 6688.95 | | 191.8 | |
| T-N-MMAF (C) | 6871.71 | 103% | 203.3 | 106% |
| T-N-MMAE (T) | 5639.24 | | 173.9 | |
| T-N-MMAE (C) | 5690.96 | 101% | 163.7 | 94% |

*Trastuzumab and T-N-MMAF were included for comparison between tests.

Figure 15:
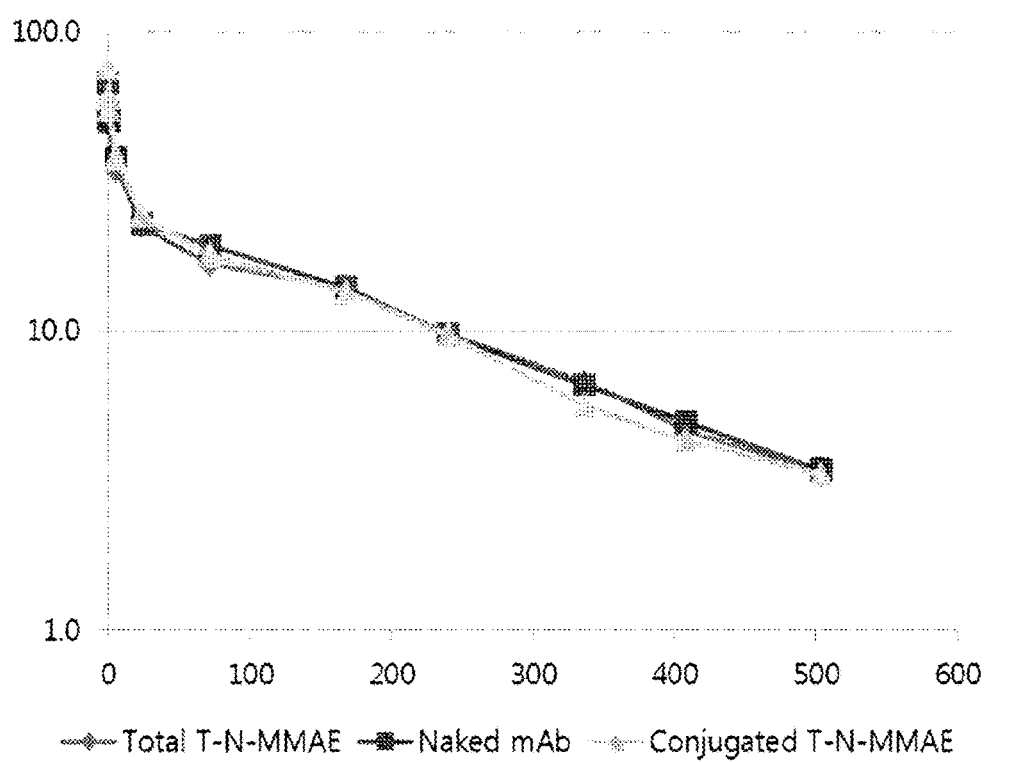
FIG. 15 shows the rat PK profile of T-N-MMAE.

As a result, as shown in FIG. 15 and Table 10 above, T-N-MMAE showed the profiles of total antibody and conjugated antibody, which did not significantly differ from that of the parent antibody, suggesting that the antibody-drug conjugate prepared using MMAE has stability similar to that of the antibody-drug conjugate prepared using MMAF.

9-1-4: Activity of T-N-MMAE

In order to determine the biological activity of the prepared MMAE conjugate, the activity thereof was measured using four different tumor cell lines. The results of the measurement are shown in Table 11 below. The method used was similar to that used in Example 5.

TABLE 11

Cytotoxicity of T-N-MMAE for HER2-expressing tumor cell lines

| | IC$_{50}$ [μM] | | |
|---|---|---|---|
| | #1 | #2 | Average |
| HCC1954 | 0.39 | 0.26 | 0.33 |
| SKOV-3 | 3.04 | 2.62 | 2.83 |
| JIMT1 | 4.00 | 3.51 | 3.76 |
| BT474 | 0.56 | 0.70 | 0.63 |

As a result, the measured IC$_{50}$ was in the range of 0.33-3.76 nM, which was similar to the activity (0.47 nM) of the BT474 cell line against the Trastuzumab/MMAE thiol conjugate reported in the literature. This suggests that the method for selective conjugation to the N-terminal α-amine according to the present invention can also be applied to other types of drugs.

9-2: Examination of Function According to Type of Antibody

In order to examine whether the method for preparing the antibody-drug conjugate according to the present invention can be applied to various antibodies, N-terminal conjugation to three anticancer antibodies (Brentuximab, Lorvotuzumab, Glembatumumab) was performed, and the DAR and in vitro stability of the conjugates were measured.

9-2-1: Brentuximab 9-2-1-1: Preparation of Brentuximab-N-MMAF

Figure 16:
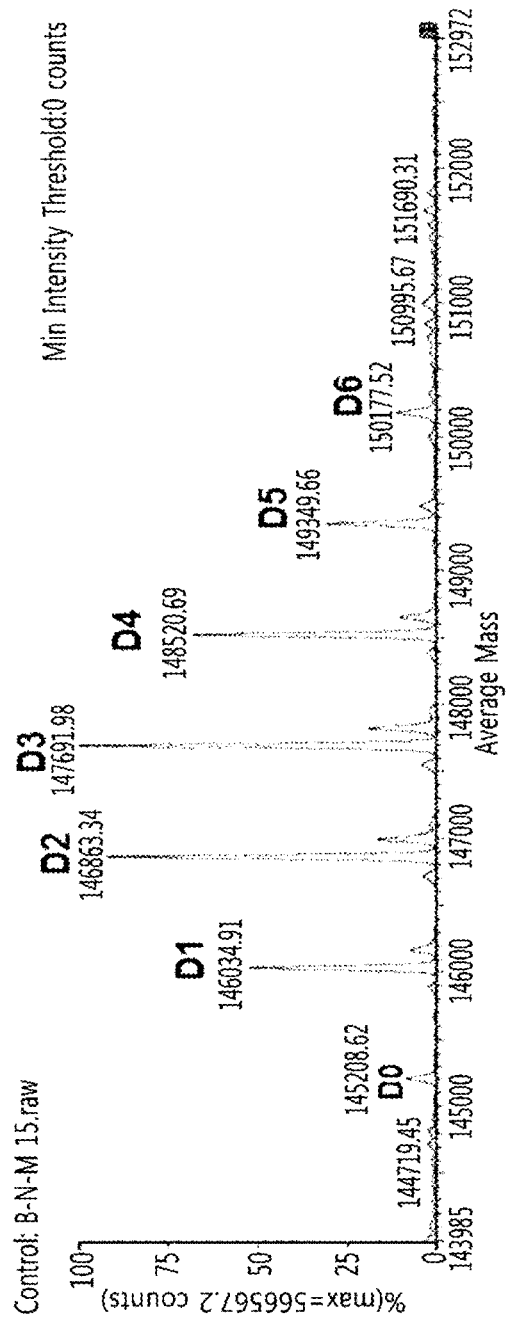
FIG. 16 shows the LC/MS profile of Brentuximab-N-MMAF (B-N-MMAF).

Using Brentuximab expressed from the CHO cell line, Brentuximab-N-MMAF (B-N-MMAF) was prepared according to the method of Example 3. The prepared ADC showed the LC/MS profile shown in FIG. 16 and Table 12 below. In the ADC, chemical species ranging from D0 to D6 were detected, and the DAR was calculated to be 2.90.

TABLE 12

| No. of bound drug | Mass (Da) | Relative content (%) | Delta mass (Da) |
|---|---|---|---|
| D0 | 145208.6 | 3.1 | |
| D1 | 146034.9 | 14 | 826.3 |

TABLE 12-continued

| No. of bound drug | Mass (Da) | Relative content (%) | Delta mass (Da) |
|---|---|---|---|
| D2 | 146863.3 | 24.4 | 828.4 |
| D3 | 147692 | 26.4 | 828.7 |
| D4 | 148520.7 | 18.2 | 828.7 |
| D5 | 149349.7 | 9.3 | 829 |
| D6 | 150177.5 | 4.7 | 827.8 |
| DAR | | 2.90 | |

9-2-1-2: Ligand Binding Assay

Figure 17:
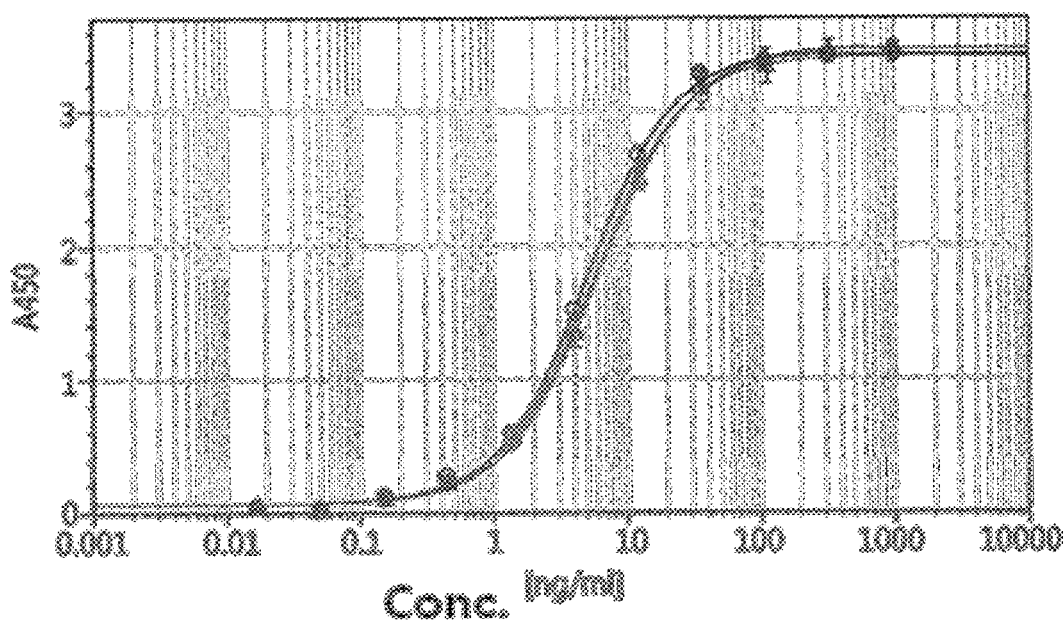
FIG. 17 shows the results of analyzing the antigen-binding activity of B-N-MMAF.

In order to determine whether the properties of the antibody are changed by conjugation, the activity of binding of the antibody to an antigen was measured by an ELISA technique. Specifically, 100 μg of the antigen CD30 (R&D Systems) was coated on a 96-well microplate, and then blocked with 1% BSA at 37° C. for 1 hour. After the blocking solution was removed, a sample was added to the plate and incubated at 37° C. for 1 hour. The plate was washed five times with PBST (PBS+0.05% tween 20), and then a 1000-fold dilution of HRP-conjugated anti-human kappa light-chain antibody was added to the plate and incubated at 37° C. for 1 hour. The plate was washed five times with PBST, and then TMB (Sigma) was added to the plate which was then subjected to color development for 10 minutes. 1N $H_2SO_4$ was added to the plate to stop the reaction, and then the absorbance of the plate at 450 nm was measured. The results of the measurement are shown in FIG. 17. In FIG. 17, the line indicated by ○ indicate results for non-conjugated Brentuximab, the line indicated by ◇ indicates results for B-N-MMAF having a DAR of 2.90, and the line indicated by Δ indicates results for B-N-MMAF having a DAR of 4.22. As can be seen from the results, the activity of binding of the antibody to the antigen did not change even after conjugation regardless of the DAR value.

9-2-1-3: In Vitro Cytotoxicity

To determine the in vitro efficacy of the prepared antibody-cytotoxin conjugate, an anti-proliferation assay was performed using Karpas-299 and L-540 cell lines that are CD30-expressing cell lines.

Specifically, each of the cell lines was cultured and suspended at a concentration of $1 \times 10^5$ cells/ml, and 100 μl of the suspension was loaded into each well of a 96-well plate. The cells were incubated in an incubator for 3 hours, and then 100 μl of the antibody-cytotoxin conjugate diluted to various concentrations was added to each well of the plate which was then incubated in an incubator for 4 days. A 1:10 dilution of CCK-8 (Dojindo) was added to each well of the plate, which was then covered with a foil and incubated in an incubator for 2-5 hours. Next, the absorbance of each well at 450 nm was measured using a SpectraMax 190 microplate reader. The results of the measurement are shown in Table 13 below.

TABLE 13

| Cell line | $IC_{50}$ (pM) |
|---|---|
| Karpas-299 | 32.2 |
| L-540 | 37.1 |

As a result, a cytotoxicity lower than 40 pM was observed in all the two cell lines (Karpas-299 and L-540).

9-2-2: Lorvotuzumab

9-2-2-1: Preparation of Lorvotuzumab-N-MMAF

Figure 18:
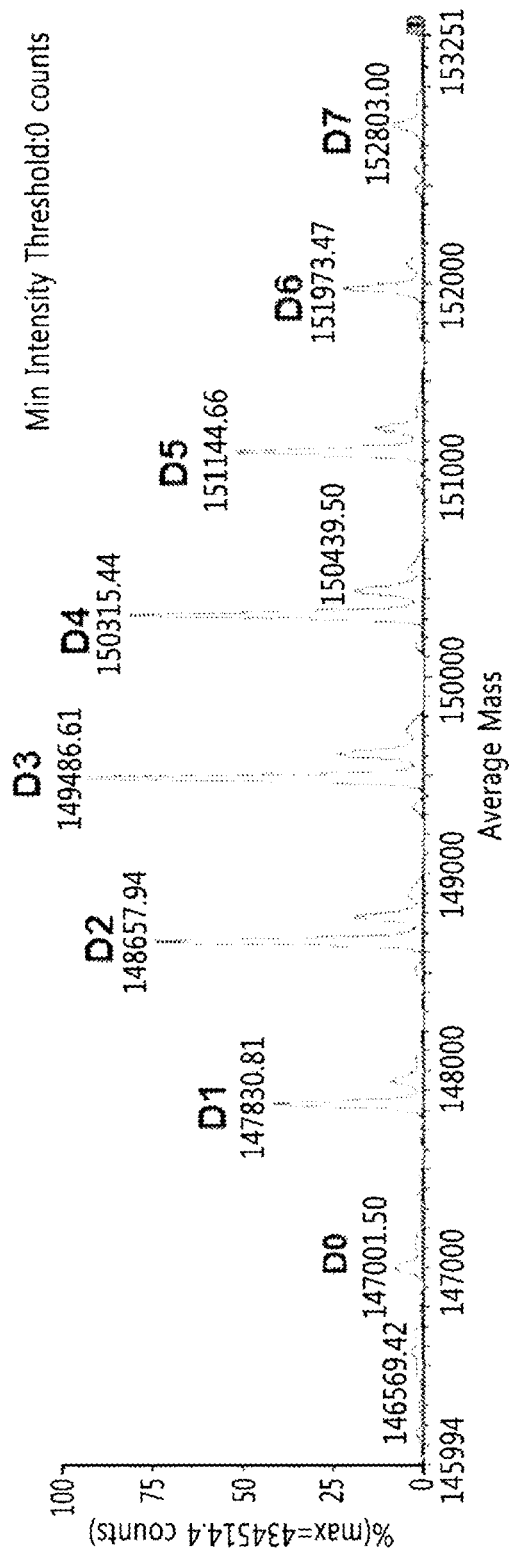
FIG. 18 shows the conjugation profile of Lorvotuzumab-N-MMAF (L-N-MMAF).

Using Lorvotuzumab expressed transiently from CHO cells, Lorvotuzumab-N-MMAF (L-N-MMAF) was prepared according to the method of Example 3. As a result, the prepared ADC showed the conjugation profile shown in FIG. 18 and Table 14 below, and the DAR of the conjugate was determined to be 3.33.

TABLE 14

| No. of bound drugs | Mass (Da) | Relative content (%) | Delta mass (Da) |
|---|---|---|---|
| D0 | 147001.5 | 3.3 | |
| D1 | 147830.8 | 10.8 | 829.3 |
| D2 | 148657.9 | 18.6 | 827.1 |
| D3 | 149486.6 | 22.7 | 828.7 |
| D4 | 150315.4 | 20.1 | 828.8 |
| D5 | 151144.7 | 13.7 | 829.3 |
| D6 | 151973.5 | 7 | 828.8 |
| D7 | 152803 | 3.7 | 829.5 |
| DAR | | 3.329 | |

9-2-2-2: Ligand Binding Assay

Figure 19:
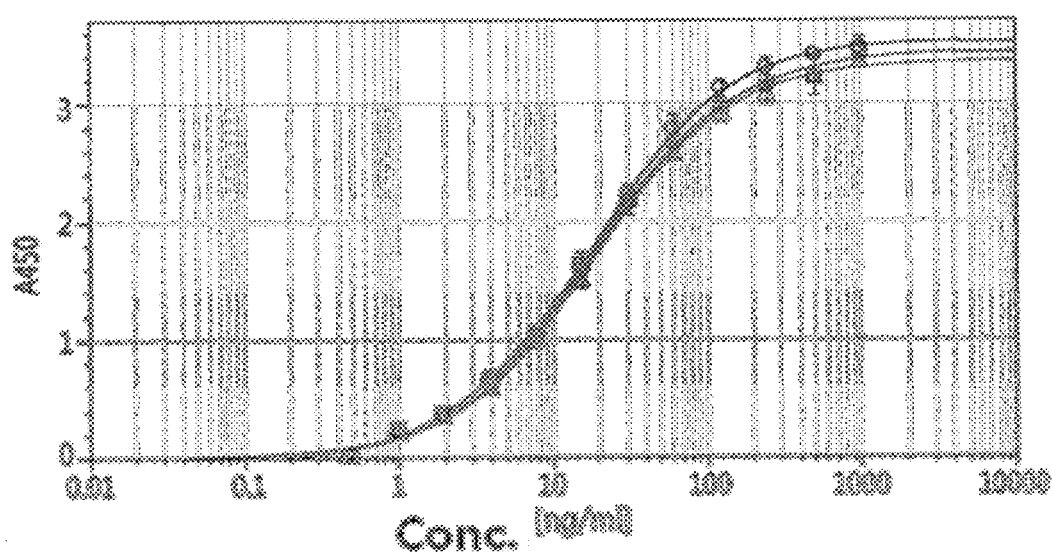
FIG. 19 shows the antigen-binding activity of L-N-MMAF.

In order to determine whether the properties of the antibody are changed by conjugation, the activity of binding of the antibody to an antigen before and after conjugation was measured by an ELISA technique. Specifically, 100 μg of the antigen CD30 (R&D Systems, 2408-NC-050) was coated on a 96-well microplate at a concentration of 1 μg/ml, and then blocked with 1% BSA at 37° C. for 1 hour. After the blocking solution was removed, a test sample was added to the plate and incubated at 37° C. for 1 hour. The plate was washed five times with PBST (PBS+0.05% tween 20), and then a 1000-fold dilution of HRP-conjugated anti-human kappa light-chain antibody was added to the plate and incubated at 37° C. for 1 hour. The plate was washed five times with PBST, and then TMB (Sigma) was added to the plate which was then subjected to color development for 10 minutes. 1N $H_2SO_4$ was added to the plate to stop the reaction, and then the absorbance of the plate at 450 nm was measured. The results of the measurement are shown in FIG. 19. In FIG. 19, the line indicated by ○ indicate results for the antibody not conjugated to the drug, the line indicated by Δ indicates results for L-N-MMAF having a DAR of 2.5, and the line indicated by ◇ indicates results for L-N-MMAF having a DAR of 3.3. As can be seen from the results, the activity of binding of the antibody to the antigen was maintained regardless of the DAR value.

9-2-2-2: In Vitro Cytotoxicity

To determine the in vitro efficacy of the prepared antibody-cytotoxin conjugate, an anti-proliferation assay was performed using an OPM-2 cell line. Specifically, the cell line was cultured and suspended at a concentration of $1 \times 10^5$ cells/ml, and 100 μl of the suspension was loaded into each well of a 96-well plate. The cells were incubated in an incubator for 3 hours, and then 100 μl of the antibody-cytotoxin conjugate diluted to various concentrations was added to each well of the plate which was then incubated in an incubator for 4 days. A 1:10 dilution of CCK-8 (Dojindo) was added to each well of the plate, which was then covered with a foil and incubated in an incubator for 2-5 hours. Next, the absorbance of each well at 450 nm was measured using a SpectraMax 190 microplate reader. The results of the measurement are shown in Table 15 below.

TABLE 15

| | IC$_{50}$ [nM] | |
|---|---|---|
| OPM-2 | L-N-MMAF DAR 2.5 | 52.9 |
| | L-N-MMAF DAR 3.3 | 41.9 |

As can be seen in Table 15 above, the L-N-MMAF antibody according to the present invention showed a cytotoxicity of about 42-53 nM.

9-2-3: Glembatumumab 9-2-3-1: In Vitro Cytotoxicity

To determine the in vitro efficacy of the prepared antibody-cytotoxin conjugate, an anti-proliferation assay was performed using a SK-MEL-2 cell line that is a skin cancer cell line. Specifically, the cell line was cultured and suspended at a concentration of 1×10$^5$ cells/ml, and 100 μl of the suspension was loaded into each well of a 96-well plate. The cells were incubated in an incubator for 3 hours, and then 100 μl of the antibody-cytotoxin conjugate diluted to various concentrations was added to each well of the plate which was then incubated in an incubator for 4 days. A 1:10 dilution of CCK-8 (Dojindo) was added to each well of the plate, which was then covered with a foil and incubated in an incubator for 2-5 hours. Next, the absorbance of each well at 450 nm was measured using a SpectraMax 190 microplate reader. The results of the measurement are shown in Table 16 below.

TABLE 16

| SK-MEL-2 | IC$_{50}$ (nM) |
|---|---|
| G-N-MMAF DAR 2.2 | 5.47 |
| G-N-MMAF DAR 3.4 | 3.36 |

As can be seen in Table 16 above, the G-N-MMAF according to the present invention showed a cytotoxicity of about 3-5 nM.

The above-described results suggest that a new platform of the antibody-drug conjugate prepared by site-specific conjugation of the drug to the N-terminal amino acid residue of the heavy chain or light chain of the antibody shows no reduction in the target specificity of the antibody while having high stability and also that the therapeutic effect of the antibody can be doubled by the drug conjugated thereto.

From the foregoing, it will be understood by those skilled in the art to which the present invention pertains that the present invention can be carried out in other concrete embodiments without changing the technical spirit or essential feature thereof. In this regard, it should be understood that the aforementioned examples are of illustrative in all aspects but not is limited. The scope of the present invention should be construed to include the meaning and scope of the appended claims, and all the alterations and modified forms which are derived from the equivalent concept thereof, rather than the detailed description.

The invention claimed is:

1. An antibody-drug conjugate comprising a cytotoxic drug conjugated to the N-terminal amino acid residue of the heavy chain or light chain of an antibody,
   wherein the cytotoxic drug is site-specifically conjugated to the N-terminal α-amine group of native first amino acid of the heavy chain or light chain of the antibody, and
   the cytotoxic drug is conjugated to the antibody by a linker having a reactive aldehyde group, and the conjugate is produced through reductive alkylation by the aldehyde group.

2. The antibody-drug conjugate of claim 1, wherein the antibody includes full-length antibodies or antibody fragments containing antigen binding domains.

3. The antibody-drug conjugate of claim 2, wherein the antibody is selected from the group consisting of IgG, scFv, Fv, Fab, Fab', and F(ab')2.

4. The antibody-drug conjugate of claim 1, wherein the cytotoxic drug is selected from the group consisting of microtubule structure formation inhibitors, meiosis inhibitors, RNA polymerase inhibitors, topoisomerase inhibitors, DNA intercalators, DNA alkylators, ribosome inhibitors, radioisotopes, and toxins.

5. The antibody-drug conjugate of claim 4, wherein the cytotoxic drug is selected from the group consisting of maytansinoid, auristatin, dolastatin, tubulysin, calicheamicin, pyrrolobenzodiazepines, doxorubicin, duocamycin, carboplatin(paraplatin), cisplatin, cyclophosphamide, ifosfamide, nidran, nitrogen mustard(mechlorethamine HCL), bleomycin, mitomycin C, cytarabine, fluorouracil, gemcitabine, trimetrexate, methotrexate, etoposide, vinblastine, vinorelbine, alimta, altretamine, procarbazine, paclitaxel, docetaxel, topotecan, irinotecan, trichothecene, CC1065, alpha-amanitin, other enediyne antibiotics, exotoxin, and plant toxin.

6. The antibody-drug conjugate of claim 5, wherein the auristatin is monomethyl auristatin E or monomethyl auristatin F.

7. The antibody-drug conjugate of claim 1, wherein the antibody binds specifically to a cancer cell surface antigen.

8. The antibody-drug conjugate of claim 7, wherein the cancer cell surface antigen is selected from the group consisting of CD19, CD20, CD30, CD33, CD37, CD22, CD56, CD70, CD74, CD138, Muc-16, mesothelin, HER2, HER3, GPNMB (glycoprotein NMB), IGF-1R, BCMA (B cell maturation antigen), PSMA (prostate-specific membrane antigen), EpCAM (Epithelial cell adhesion molecule), and EGFR (epidermal growth factor receptor).

9. The antibody-drug conjugate of claim 1, wherein the antibody is selected from the group consisting of an anti-HER2 antibody, an anti-CD30 antibody, an anti-CD56 antibody, and an anti-GPNMB (glycoprotein NMB) antibody.

10. The antibody-drug conjugate of claim 9, wherein the antibody is selected from the group consisting of Trastuzumab, Lorvotuzumab, Brentuximab, and Glembatumumab.

11. A pharmaceutical composition for treating cancer, which comprises the antibody-drug conjugate of claim 1.

* * * * *

UNITED STATES PATENT AND TRADEMARK OFFICE
CERTIFICATE OF CORRECTION

PATENT NO. : 10,071,170 B2
APPLICATION NO. : 14/898126
DATED : September 11, 2018
INVENTOR(S) : Young Min Kim et al.

It is certified that error appears in the above-identified patent and that said Letters Patent is hereby corrected as shown below:

In the Specification

Column 15, Line 14: "10440" should be -- T0440 --.

Signed and Sealed this
Twenty-third Day of October, 2018

Andrei Iancu
*Director of the United States Patent and Trademark Office*